(12) United States Patent
de Lacharriere et al.

(10) Patent No.: US 7,366,707 B2
(45) Date of Patent: Apr. 29, 2008

(54) METHODS INVOLVING ARTIFICIAL INTELLIGENCE

(75) Inventors: Olivier de Lacharriere, Paris (FR);
Philippe Bastien, Charenton le Pont (FR); Fouad Badran, Paris (FR);
Sylvie Thiria, Paris (FR)

(73) Assignee: L'Oreal S.A., Paris (FR)

( * ) Notice: Subject to any disclaimer, the term of this patent is extended or adjusted under 35 U.S.C. 154(b) by 787 days.

(21) Appl. No.: 10/446,926

(22) Filed: May 29, 2003

(65) Prior Publication Data

US 2004/0034610 A1 Feb. 19, 2004

Related U.S. Application Data

(60) Provisional application No. 60/383,812, filed on May 30, 2002.

(51) Int. Cl.
*G06F 15/00* (2006.01)
*G06F 15/18* (2006.01)
(52) U.S. Cl. ..................................... 706/62
(58) Field of Classification Search ................ 706/12, 706/62
See application file for complete search history.

(56) References Cited

U.S. PATENT DOCUMENTS

| | | | |
|---|---|---|---|
| 6,564,197 B2* | 5/2003 | Sahami et al. | 706/55 |
| 6,938,027 B1* | 8/2005 | Barritz et al. | 706/50 |
| 7,082,418 B2* | 7/2006 | Levy et al. | 706/12 |
| 2003/0065524 A1* | 4/2003 | Giacchetti et al. | 705/1 |
| 2003/0110253 A1* | 6/2003 | Anuszczyk et al. | 709/224 |
| 2003/0130975 A1* | 7/2003 | Muller | 706/50 |

* cited by examiner

*Primary Examiner*—Michael B. Holmes
(74) *Attorney, Agent, or Firm*—Finnegan, Henderson, Farabow, Garrett & Dunner, L.L.P.

(57) ABSTRACT

One aspect of the present invention relates to methods of generating a profile data set. In an exemplary embodiment, data is accessed and the accessed data is processed using a dynamic cluster method, mobile center method, and/or a k-means algorithm, each using neighborhood data. Other aspects relate to methods of generating a diagnosis, advice, and/or other information. Further aspects relate to dynamic surveying and systems.

34 Claims, 18 Drawing Sheets

SURVEY

Please follow these instructions when filling out this questionnaire:
- Use a ballpoint pen to fill out this questionnaire.
- Answer all questions.
- If no category matches your condition exactly, select the answer that most closely resembles it.

Identification Number |__|__|__|__|__|__|   Four-letter Code|__|__|__|__|
Age |__|__|
Smoke        Yes ☐  No ☐
Date (questionnaire was answered) |__|__| |__|__| |__|__|   Birth year |__|__|
Gender    M ☐ F ☐                            day    month   year

1. Which of the following points best describe your hair?
(Check the box(es) that applies to you. You may check more than one box.)

| | | | |
|---|---|---|---|
| Hair loss. . . . . . . . . . . . . . .Yes ☐ No ☐ | | Difficulty styling hair . . . . . Yes ☐ No ☐ |
| White hair . . . . . . . . . . . . .Yes ☐ No ☐ | | Dry hair. . . . . . . . . . . . . . Yes ☐ No ☐ |
| Dandruff . . . . . . . . . . . . . .Yes ☐ No ☐ | | Split ends . . . . . . . . . . . . . Yes ☐ No ☐ |
| Oily hair. . . . . . . . . . . . . . .Yes ☐ No ☐ | | Dull hair . . . . . . . . . . . . . Yes ☐ No ☐ |
| Fragile or brittle hair. . . . . .Yes ☐ No ☐ | | Sensitive scalp . . . . . . . . . Yes ☐ No ☐ |
| Thinning hair. . . . . . . . . . .Yes ☐ No ☐ | | Total or partial baldness . . . . Yes ☐ No ☐ |
| (decreasing hair density) | | (absence of hair on an area of the head) |

2. Which of the following points have you consulted a physician about during your lifetime?
(Check the box(es) that applies(y) to you. You may check more than one box.)

Hair loss. . . . . . . . . . . . . . .Yes ☐ No ☐     Difficulty styling hair . . . . . Yes ☐ No ☐
White hair . . . . . . . . . . . . .Yes ☐ No ☐      Dry hair. . . . . . . . . . . . . . Yes ☐ No ☐
Dandruff . . . . . . . . . . . . . .Yes ☐ No ☐      Split ends . . . . . . . . . . . . . Yes ☐ No ☐
Oily hair. . . . . . . . . . . . . . .Yes ☐ No ☐     Dull hair . . . . . . . . . . . . . Yes ☐ No ☐
Fragile or brittle hair. . . . . .Yes ☐ No ☐         Sensitive scalp . . . . . . . . . Yes ☐ No ☐
Thinning hair. . . . . . . . . . .Yes ☐ No ☐         Total or partial baldness . . . . Yes ☐ No ☐
(decreasing hair density)                            (absence of hair on an area of the head)

3. How frequently do you wash your hair? (Check only one box)
Less than once a week. . . . . . . . . . . . ☐       Four to five times a week . . . . . . . . . ☐
Once a week. . . . . . . . . . . . . . . . . . ☐     Six to seven times a week . . . . . . . . . ☐
Two to three times a week. . . . . . . . . ☐         More than once a day . . . . . . . . . . . . ☐

•
•
•

42. Which of the following fingernail care treatments do you use:
(Check at least one box per line)

|  | Rarely | Often | Not at all |
|---|---|---|---|
| Treatment at specialized institutes. . . . . | ☐ | ☐ | ☐ |
| Hardener . . . . . . . . . . . . . . . . . . . | ☐ | ☐ | ☐ |
| Protective base. . . . . . . . . . . . . . . | ☐ | ☐ | ☐ |
| Softener (moisturizer) . . . . . . . . . . | ☐ | ☐ | ☐ |
| Nourishing cream and/or oil. . . . . . . . | ☐ | ☐ | ☐ |
| Multivitamin treatment . . . . . . . . . . | ☐ | ☐ | ☐ |
| Smoothing treatment. . . . . . . . . . . . | ☐ | ☐ | ☐ |
| Nail polish. . . . . . . . . . . . . . . . . | ☐ | ☐ | ☐ |

43. Which of the following haircare treatments do you use:
(Check at least one box per line)

|  | Rarely | Often | Not at all |
|---|---|---|---|
| Permanent (or ["body wave"]). . . . . . . . | ☐ | ☐ | ☐ |
| Permanent hair color (dye) . . . . . . . . | ☐ | ☐ | ☐ |
| Temporary color (washes out in 6 to 8 shampoos) . . . . . . | ☐ | ☐ | ☐ |
| Hair bleaching (or "highlights") . . . . . . | ☐ | ☐ | ☐ |
| Hair mask. . . . . . . . . . . . . . . . . . | ☐ | ☐ | ☐ |
| Conditioner (or detangler) . . . . . . . . | ☐ | ☐ | ☐ |
| Styling gel or mousse. . . . . . . . . . . | ☐ | ☐ | ☐ |
| Hood-type hair drier or blow-drying. . . . | ☐ | ☐ | ☐ |

Thank You For Taking The Time To Fill Out This Questionnaire

FIG. 2

LIST OF QUERIES AND QUERY ANSWERS

Are you a? Man=1, Woman= 0
    'Man'

Concerned about hair loss? yes=1, no=0
    'No'

Concerned about white hair? yes=1, no=0
    'Yes'

Concerned about dandruff? yes=1, no=0
    'No'

Do you smoke? yes=1, no=0
    'No'

Concerned about partial or total baldness? yes=1, no=0
    'No'

Do you think that your hair coarseness is for the most part:
| | |
|---|---|
| very fine | TYPE 1 |
| fine | TYPE 2 |
| average | TYPE 3 |
| thick coarse | TYPE 4 |
| very thick, very coarse | TYPE 5 |

Your answer: 2

'Fine hair'

What was the natural color of your hair at age 18:
| | |
|---|---|
| Red | TYPE 1 |
| Platinum blonde | TYPE 2 |
| Golden blonde | TYPE 3 |
| Light chestnut brown | TYPE 4 |
| Dark chestnut brown | TYPE 5 |
| Brown | TYPE 6 |
| Black | TYPE 7 |

Your answer: 1

'Red hair'

FIG. 3A

DIAGNOSED CHARACTERISTICS KNOWN BUT NOT
PROVIDED BY DURANT LAURENT

'Washes hair 2 to 3 times per week'
'you lose little or none during washing'
'you lose little or none on towel'
'Little or no loss during brushing'
'Little or no hair on pillow'
'Little or no hair on clothing'
'I lose my hair but normal phenomenon'
'I don't have abnormal hair loss'
'Hair density average on temples'
'Hair density average on top of head'
'Hair density decreased slightly with age'
'Father late full hair'
'Mother late full hair'
'Grandfather late full hair'
"Salt and pepper hair (gray)'
'White hair apparent between 46 and 50 years old'
'Natural hair color light chestnut brown'
'Hair naturally supple or wavy'
'My eyes are green or hazel'
'I have light skin'
'I think I am moderately hairy'
'I am quite calm'
'My hair is not oily'
'I don't have dandruff'
'I have very hard nails'
'The people around you find you nervous'
'I am over age 56'
'I am from Ile-de-France'
'Body Mass Index (BMI) overweight'

FIG. 3B

DIAGNOSED CHARACTERISTICS UNKNOWN AND NOT
PROVIDED BY DURANT LAURENT

'493<Chol<743 (mmol/L)'
'0.62<Trigly<2.47'
'Glycemia>61 (mmol/L)'
'Ferrit>20 woman Ferrit>90 man'
'M_tas96>123.6'
'M_tad=79.6'
'Anxiety score above average'
'Depression score above average'

FIG. 3C

LIST OF QUERIES AND QUERY ANSWERS

Are you a? Man=1, Woman= 0[1]
    'Woman'
Concerned about hair loss? yes=1, no=0
    'Yes'
Concerned about white hair? yes=1, no=0
    'No'
Concerned about dandruff? yes=1, no=0
    'No'
Concerned about oily hair? yes=1, no=0
    'No'
Concerned about fragile or brittle hair? yes=1, no=0
    'Yes'
Do you smoke? yes=1, no=0
    'Yes'
Concerned about split ends? yes=1, no=0
    'No'

FIG. 3D

DIAGNOSED CHARACTERISTICS KNOWN BUT NOT
PROVIDED BY YOLANDA LAUEX

'Concerned about dull hair'
'Wash 2 to 3 times per week'
'you lose little or none during washing'
'you lose little or none on towel'
'Little or no loss during brushing'
'Little or no hair on pillow'
'Little or no hair on clothing'
'I lose my hair but normal phenomenon'
'I don't have abnormal hair loss'
'Already followed treatment'
'Treatment lotion'
'Other treatments'
'Very fine hair'
'Hair density low on temples'
'Hair density low on top of head'
'Hair density decreased slightly with age'
'$F^1$ early hair loss'
'Father G-F late full hair'
'Mother G-F late full hair'
'No or very few white hairs'
'White hair apparent between 41 and 45 years old'
'Father G-M late without white hair'
'Father G-F late without white hair'
'Natural hair color light chestnut brown'
'Hair naturally straight'
'My eyes are brown or [light] brown'
'I have light skin'
'I think I am moderately hairy'
'I am quite stressed'
'My hair is not oily'
'I have little dandruff'
'I have nails that split'
'I have very hard nails'
'My profession is a [Manager]'
'Concerned thinning hair'
'Number cigarettes per day= 16/20'
'Length of time smoked= 21/30 years'
'Smoke inhalation'
'Brittle hair'
'Hair falls out easily'
'The people around you find you nervous'
'memory problems'
'sensitive to cold'
'I am between 46 and 50 years old'
'I am from Ile-de-France'
'Body Mass Index (BMI) overweight'

FIG. 3E

DIAGNOSED CHARACTERISTICS UNKNOWN AND NOT
PROVIDED BY YOLANDA LAUEX

'493<Chol<743 (mmol/L)'
'0.62<Trigly<2.47'
'3.9<Glycemia<6.1'
'Ferrit>20 woman Ferrit>90 man'
'M_tas96>123.6'
'M_tad=79.6'
'Anxiety score below average'
'Depression score above average'

FIG. 3F

ADDITIVE BINARY ENCODING

| Modality | Encoding | Qualitative Information |
|----------|----------|-------------------------|
| 1 | 1 0 0 | Rare |
| 2 | 1 1 0 | Often |
| 3 | 1 1 1 | Not at all |

FIG. 5

DISJUNCTIVE BINARY ENCODING

| Modality | Encoding |
|----------|----------|
| 1 | 1 0 0 0 |
| 2 | 0 1 0 0 |
| 3 | 0 0 1 0 |
| 4 | 0 0 0 1 |

FIG. 6

| Label | Characteristic | Modality | Encoding | Qualitative Information |
|---|---|---|---|---|
| a | gender | 1 | 1 | Male |
|   |   | 2 | 0 | Female |
| b | concern about hair loss | 1 | 1 | Yes |
|   |   | 2 | 0 | No |
| c | concern about white hair | 1 | 1 | Yes |
|   |   | 2 | 0 | No |
| d | concern about dandruff | 1 | 1 | Yes |
|   |   | 2 | 0 | No |
| e | smoke | 1 | 1 | Yes |
|   |   | 2 | 0 | No |
| f | concern about baldness | 1 | 1 | Yes |
|   |   | 2 | 0 | No |
| g | hair coarseness | 1 | 10000 | Very fine |
|   |   | 2 | 01000 | Fine |
|   |   | 3 | 00100 | Average |
|   |   | 4 | 00010 | Thick, Coarse |
|   |   | 5 | 00001 | Very Thick, Very Coarse |
| h | natural hair color | 1 | 1000000 | Red |
|   |   | 2 | 1100000 | Platinum blonde |
|   |   | 3 | 1110000 | Golden blonde |
|   |   | 4 | 1111000 | Light chestnut blonde |
|   |   | 5 | 1111100 | Dark chestnut blonde |
|   |   | 6 | 1111110 | Brown |
|   |   | 7 | 1111111 | Black |

FIG. 7A

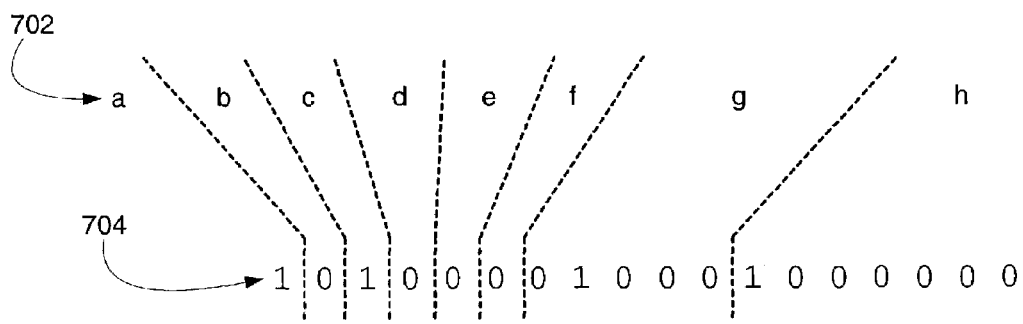

FIG. 7B

$z_4 \rightarrow$ 1 0 1 1 0 0 0 1 0 0 0 1 0 0 0 0 0
$z_5 \rightarrow$ 0 0 1 1 1 0 0 0 1 0 0 1 1 1 0 0 0 0
$z_6 \rightarrow$ 0 1 0 0 1 0 0 0 1 0 0 1 1 1 1 0 0 0
$z_7 \rightarrow$ 0 1 0 0 1 0 0 0 0 1 0 1 1 1 1 0 0 0
$z_{10} \rightarrow$ 0 1 0 0 1 0 0 1 0 0 0 1 1 1 1 0 0 0
$z_{13} \rightarrow$ 1 0 1 0 0 0 0 0 1 0 0 1 1 1 1 1 1 1
$z_{21} \rightarrow$ 1 1 0 1 0 1 0 0 0 0 1 1 1 1 1 0 0 0

$r \rightarrow$ 0 1 0 0 1 0 0 0 0 0 0 1 1 1 1 0 0 0

FIG. 10

METHODS INVOLVING ARTIFICIAL INTELLIGENCE

This application claims benefit of priority to U.S. provisional patent application No. 60/383,812, filed on May 30, 2002.

FIELD OF THE INVENTION

Aspects of the present invention relate to methods, combinations, apparatus, systems, and articles of manufacture for generating a profile data set and/or for generating a diagnosis, advice, and/or other information. In another aspect, the invention may include dynamic surveying. Certain exemplary embodiments may involve data organized by an artificial intelligence engine.

BACKGROUND OF THE INVENTION

Traditional diagnostic methods are often inconvenient, labor intensive, and expensive because they require in-depth analysis by trained experts. In the realm of personal diagnosis, for example, a subject suffering from an illness or other health condition typically has to visit a medical professional to diagnose his/her condition. This may require scheduling an appointment with the professional, traveling to the professional's office, waiting to be seen by the professional, finally being examined, and possibly returning to the office for subsequent examinations. The examination itself may require the subject to answer many questions and perform a large battery of tests before a proper diagnosis is obtained. Many times this process may require more effort and be more expensive than the subject is willing to accept. Accordingly, the subject may choose to not bother with the diagnosis. Thus, a convenient means for the subject to obtain a preliminary diagnosis from a remote location without answering an overwhelming number questions would be beneficial.

In aspects outside of personal diagnosis, traditional analysis typically involves collecting empirical data, distilling the data, and drawing conclusions from the data, wherein the conclusions may be used in the future for diagnostic purposes. In order to make correct diagnoses from these conclusions, often a large quantity of initial empirical data may be required. Large amounts of data compound the problem of distilling and analyzing the data. As a result, highly skilled individuals must spend valuable time collecting, organizing, and interpreting the data to glean useful information from it.

In another diagnosis example in the field of chemical analysis, a researcher searching for unique properties of chemical compounds (or chemical compounds having such properties) may conduct numerous experiments and collect a massive quantity of data. In order for the researcher to extract useful information from the data, he/she has to perform the tedious task of organizing and evaluating the experimental results. Therefore, it would be beneficial to provide a means to organize data quickly and accurately. Once data is properly organized, the researcher may find the data useful, in at least the chemical analysis example, to diagnose properties of additional samples.

Although the foregoing background discussion is directed primary to diagnostics, it will become apparent in the following description that many aspects of the present invention have applicability in fields other than those involving a diagnosis. Accordingly, the background discussion should be considered to be exemplary of a few of many possible background issues that could be addressed.

SUMMARY OF A FEW EXEMPLARY ASPECTS OF THE INVENTION

Methods, combinations, apparatus, systems, and articles of manufacture consistent with features and principles of the present invention may generate a profile data set; generate a diagnosis, advice, and/or other information; and/or perform dynamic surveying.

One exemplary aspect of the present invention may include a method of generating a profile data set. The method may comprise accessing data and processing the accessed data using at least one of a dynamic cluster method and a k-means algorithm to generate profiles for the profile data set. The accessed data may comprise qualitative data. The dynamic clustering method and/or k-means algorithm may use neighborhood data.

A second exemplary aspect of the present invention may include a diagnostic method. The diagnostic method may comprise accessing data organized by an artificial intelligence engine, receiving information reflecting that a sample exhibits a first group of characteristics, and processing the received information and the accessed data. The accessed data may be about a plurality of groups of characteristics and may comprise at least one link between at least the first group of the plurality of groups and a second group of the plurality of groups. The processing may generate a diagnosis reflecting the sample's predisposition to exhibit the second group of characteristics.

A third exemplary aspect of the present invention may include a dynamic survey method. The method may comprise accessing data organized by an artificial intelligence engine, accessing queries, and presenting to a subject a subset of queries from the accessed queries. The answers to at least some of the queries may be used to process at least some of the accessed data. For at least some of the queries presented, the method may further comprise selecting a next query as a function of the subject's answer to a previous query.

A fourth exemplary aspect of the present invention may include a method of generating a profile data set. The method may comprise accessing data about a plurality of groups of characteristics, processing the accessed data to generate binary encoded data representing modalities of the characteristics, processing the binary encoded data to generate profiles for the profile data set, and assigning at least some of at least one of the plurality of groups, the accessed data, and the binary encoded data to the profiles to generate the profile data set. Accessing, processing, and/or assigning may use an artificial intelligence engine.

A fifth exemplary aspect of the present invention may include a diagnostic method comprising accessing a plurality of queries, presenting to a subject a subset of queries from the accessed queries, receiving information reflecting the subject's answer to each presented query, accessing data about a plurality of groups of characteristics exhibited by a plurality of individuals, and processing the received information and the accessed data. The data may comprise at least one link between at least a first group of the plurality of groups and a second group of the plurality of groups. At least one query answer of the subject may reflect that the subject exhibits the first group of characteristics. For at least some of the queries presented, the method may further comprise selecting a next query as a function of the subject's answer to a previous query. The processing may generate a diagnosis reflecting the subject's predisposition to exhibit the second group of characteristics.

A sixth exemplary aspect of the present invention may include a method of generating advice. The method may comprise accessing data organized by an artificial intelligence engine, receiving information reflecting that a subject exhibits the first group of characteristics, and processing the received information and the accessed data. The data may be about a plurality of groups of characteristics and may comprise at least one link between at least a first group of the plurality of groups and a second group of the plurality of groups. The processing may generate advice related to the subject's predisposition to exhibit the second group of characteristics.

A seventh exemplary aspect of the present invention may include a method of generating information related to at least one blood characteristic. The method may comprise accessing data comprising blood characteristic data and hair characteristic data for a plurality of respective individuals, receiving information reflecting at least one hair characteristic of a subject, and processing the received information and the accessed data. The processing may generate information related to the subject's predisposition to exhibit at least one blood characteristic.

A further aspect may relate to systems including structure configured to perform one or more methods disclosed herein.

Additional aspects of the invention are set forth in the description which follows and, in part, are obvious from the description, or may be learned by practice of methods, combinations, devices, systems, and articles of manufacturer consistent with features of the present invention. It is understood that both the foregoing description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several aspects of the invention and, together with the description, serve to explain exemplary principles of the invention. In the drawings.

FIG. 2 illustrates an exemplary survey consistent with features and principles of the present invention;

FIG. 3A illustrates a first exemplary list of queries and query answers consistent with features and principles of the present invention;

FIG. 3B illustrates a first exemplary diagnosis for a first subject consistent with features and principles of the present invention;

FIG. 3C illustrates a second exemplary diagnosis for the first subject consistent with features and principles of the present invention;

FIG. 3D illustrates a second exemplary list of queries and query answers consistent with features and principles of the present invention;

FIG. 3E illustrates a first exemplary diagnosis for a second subject consistent with features and principles of the present invention;

FIG. 3F illustrates a second exemplary diagnosis for the second subject consistent with features and principles of the present invention;

FIG. 5 illustrates an exemplary table of modalities using additive binary coding consistent with features and principles of the present invention;

FIG. 6 illustrates an exemplary table of modalities using disjunctive binary coding consistent with features and principles of the present invention;

FIG. 7A illustrates an exemplary table of modalities for a group of characteristics consistent with features and principles of the present invention;

FIG. 7B illustrates an exemplary binary encoded data consistent with features and principles of the present invention;

FIG. 10 illustrates an exemplary center median calculation consistent with features and principles of the present invention;

DESCRIPTION OF EXEMPLARY EMBODIMENTS

Figure 1:
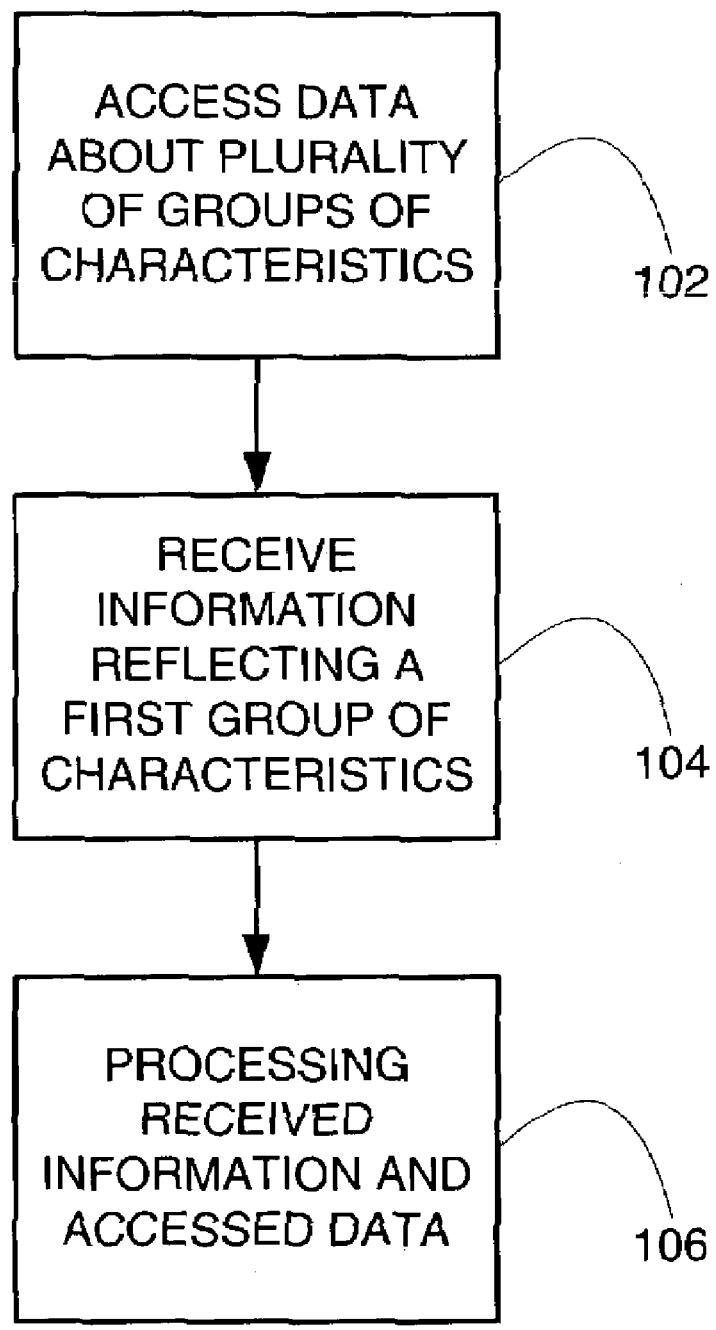
FIG. 1 illustrates an exemplary flow chart for a diagnostic method consistent with features and principles of the present invention.

Reference is now made in detail to exemplary embodiments of the invention, examples of which are illustrated in the accompanying drawings. Wherever possible, the same reference numbers may be used in the drawings to refer to the same or like parts.

The exemplary embodiments described herein are primarily related to diagnostic methods involving subject individuals and certain individual characteristics relating to beauty, personal habits, blood chemistry, etc. However, it should be understood that the method, in a broader sense, could involve numerous other types of individual characteristics, and, furthermore the invention could be practiced to provide diagnoses of samples other than individuals. In addition, it should be understood that certain aspects of the invention have applicability in fields other than those involving a diagnosis.

One embodiment of the invention may include a diagnostic method. The method may be used to generate a diagnosis reflecting a sample's predisposition to exhibit a group of characteristics. The sample may be at least one of a subject individual, chemical, molecule, item, location, idea, and/or any other subject of interest to be diagnosed. Characteristics may include physical, medical, physiological, biological, chemical, molecular, beauty, situational, and/ or any other characteristic. A group of characteristics may include one or more characteristics. The diagnosis of the sample's predisposition may include a likelihood (and/or unlikelihood) that the sample currently exhibits, has exhibited in the past, and/or will exhibit in the future, one or more characteristics in the group.

Examples of characteristics that could be involved in a diagnosis of a subject individual may include fashion preferences, demographic, nutrition, cosmetic usage, medical history, environment, beauty product usage, lifestyle, name, age, birth date, height, weight, ethnicity, eating habit, blood (e.g., type, chemistry, etc.), hair condition, vacation pattern, geographic location of the individual's residence, location, work, work habit, sleep habit, toiletries used, exercise habit, relaxation habit, beauty care habit, smoking habit, drinking habit, sun exposure habit, use of sunscreen, propensity to tan, number of sunburns and serious sunburns, dietary restriction, dietary supplement or vitamin used, diagnosed condition affecting the external body, such as melanoma, facial feature, family history, such as physical characteristics about relatives of the individual (e.g., premature balding, graying, wrinkles, etc.), external body condition, color preference, clothing style preference, travel habit, entertainment preference, fitness information, adverse reaction to products, adverse reaction to compounds, adverse reaction to elements (e.g., sun exposure), body chemistry, purchasing habit, shopping habit, browsing habit, hobby, marital status, parental status, number of children, country of residence, region of residence, birth country and region, religious affiliation, political affiliation, whether the individual is an urban dweller, suburban dweller, or rural area dweller, size of urban area in which the subject lives, whether the individual is retired, annual income, sexual preference, or any other characteristic.

Blood characteristics may include any condition related to the circulatory system of a living being (e.g., heart attack, stroke, blood pressure, anemia, blood chemistry, blood type, etc.).

According to features and principles consistent with the invention, an embodiment of the invention may access data about a plurality of groups of characteristics, as illustrated at step 102 in the flow chart of FIG. 1. Accessing data may include receiving/obtaining data from a database, data structure, storage medium, survey, and/or any other mechanism or combination of mechanisms. The accessed data may be raw data, such as data entries from a database, preprocessed data, such as encoded raw data, or any other form of data. "Accessing" data may include at least one of acquisition via a network, via verbal communication, via electronic transmission, via telephone transmission, in hard-copy form, or through any other mechanism enabling acquisition or reception of data. In addition, "accessing" may occur either directly or indirectly. For example, receipt may occur through a third party acting on another party's behalf, as an agent of another, or in concert with another. Regardless, all such indirect and direct actions are intended to be covered by the term "accessing" as used herein.

Accessed data, for example, may take one of many forms. It may simply be a checked box, clicked button, submitted form, or oral affirmation. Or it might be typed or handwritten textual data. Accessing may occur through an on-line form, e-mail, facsimile, telephone, interactive voice response system, or file transfer protocol transmitted electronically over a network at a web site, an Internet Protocol address, or a network account. Data may be accessed from a subject for whom information is sought, or an entity acting on the subject's behalf. Receipt may occur physically such as in hard copy form, via mail delivery, or other courier delivery.

"Accessing" may involve receipt directly or indirectly through one or more networks and/or storage mediums. Examples of storage media may include magnetic storage devices such as floppy disks and hard drives, optical storage devices, such as compact discs and digital video discs, organic storage devices, electronic storage devices, random access memory, virtual memory, permanent memory, printed media, and/or any other medium for storing information.

The term "network" may include a public network such as the Internet or a telephony network, a private network, a virtual private network, or any other mechanism for enabling communication between two or more nodes or locations. The network may include one or more of wired and wireless connections. Wireless communications may include radio transmission via the airwaves, however, those of ordinary skill in the art will appreciate that various other communication techniques can be used to provide wireless transmission including infrared line of sight, cellular, microwave, satellite, blue-tooth packet radio and spread spectrum radio. Wireless data may include, but is not limited to, paging, text messaging, e-mail, Internet access and other specialized data applications specifically excluding, or including voice transmission.

In some instances consistent with the invention, a network may include a courier network (e.g. postal service, United Parcel Service, Federal Express, etc.). Other types of networks that are to be considered within the scope of the invention include local area networks, metropolitan area networks, wide area networks, ad hoc networks, or any mechanism for facilitating communication between two nodes or remote locations.

It should be noted that the terms "network" and "neural network", as used herein, have distinct meanings. A "neural network" may be any organization of "neurons" associated with one or more algorithms, and/or may have any other configuration known in the art of artificial intelligence. Accordingly, a "neural network" may or may not be associated with a "network".

The data accessed in step 102 of FIG. 1 may be data that has been organized as a result of processing using an artificial intelligence engine. As described in more detail below, one example of a data organization includes a profile data set resulting from a neural network using one or more types of algorithms. However, it should be understood that there are many other alternative ways in which the data may be organized.

The accessed data may be based on information previously collected in any known manner. For example, when the method involves diagnosis of one or more individuals, FIG. 2 illustrates an exemplary survey that may be used to collect characteristic information for a plurality of individuals. Results of the survey for a plurality of individuals may be optionally encoded, organized using an artificial intelligence engine, and stored in a database or other storage mechanism that may be accessed, as described above. The survey may contain queries about many characteristics of an individual and may be completed over the Internet. The characteristics for a particular individual may include any characteristic as described above. In this example, the survey may contain queries about gender, smoking habit, occurrence of hair loss, occurrence of white hair (i.e., senescent hair, such as whitened or gray hair), occurrence of dandruff, concern about hair loss, concern about white hair, concern about dandruff, concern about baldness, coarseness of hair, color of hair, frequency of use of fingernail hardener, frequency of use of fingernail multivitamin treatment, frequency of use of nail polish, frequency of use of hair treatments, etc.

For each individual completing the survey of FIG. 2, there could be additional information collected about the individual. Such additional information could be information that is not normally known by an individual and/or information that is only known after performing a particular test, examination, and/or analysis. For example, for each of the individuals completing the survey of FIG. 2, there could be a collection of additional information relating to blood chemistry, anxiety test score, depression test score, and/or any other information normally requiring some form of test, examination, and/or analysis in order to be revealed. The additional information could optionally be encoded and stored in a database or other storage medium that may be accessed, as described above.

Some of the characteristics may be grouped into a first group of characteristics (e.g., the first group of characteristics may include gender, concern about hair loss, concern about white hair, concern about dandruff, smoking habit, concern about baldness, coarseness of hair, and color of hair). The grouping may be performed through an expert determination, algorithm, artificial intelligence, or other mechanism. The grouping may be performed prior to accessing data, wherein accessing receives data reflecting previously grouped characteristics. Alternatively, the grouping may take place, at least partially, after the data is accessed. The grouping may be used to isolate characteristics that may predict the exhibition of other characteristics by the individual. For example, the grouping may be performed by an analyst wishing to diagnose a subject individual based on the first group of characteristic information from other individuals.

Other characteristics may be grouped into a second group of characteristics (e.g., the second group of characteristics may include occurrence of hair loss and frequency of use of a fingernail multivitamin treatment) as previously described. Additional groups of characteristics may be formed and any group of characteristics may contain the same characteristic as another group of characteristics.

As stated previously, the data about the characteristics may be from many sources other than or in conjunction with the survey response (e.g., the data may include blood characteristics from a medical databank) and the accessed data may be partially processed using some mechanism, such as an artificial intelligence engine. Partial processing may include binary encoding as described later.

The accessed data may include at least one link between at least the first group of a plurality of groups and the second group of the plurality of groups. The link may indicate exhibition of the first group of characteristics by a sample implies likely or unlikely exhibition of the second group of characteristics by the sample. For example, a link may exist between a first group of characteristics listed in FIG. 3A and a second group of characteristics listed in FIGS. 3B and 3C, such that a subject individual exhibiting the characteristics in FIG. 3A may be diagnosed to exhibit the characteristics in FIGS. 3B and 3C. Alternatively, the link may indicate exhibition of the first group of characteristics by a sample implies unlikely exhibition of the second group of characteristics by the sample. For example, a link may exist between a first group of characteristics listed in FIG. 3A and a second group of characteristics listed in FIGS. 3B and 3C, such that a subject individual exhibiting the characteristics in FIG. 3A may be diagnosed to not exhibit all the characteristics in FIGS. 3B and 3C. Further, the link may indicate that any one group or combination of groups of characteristics implies likely or unlikely exhibition of any other group or groups of characteristics. Also, the link may be accessed via any of the mechanisms described above, previously generated, generated at a time data is accessed, and/or stored via any of the storage media listed above. As described later herein, the link may be generated using artificial intelligence.

An embodiment consistent with features and principles of the invention may receive information reflecting a sample exhibiting the first group of characteristics, as illustrated at step 104 in the flow chart of FIG. 1. The information may be received in any manner as described above in association with data accessing. For example, FIG. 3A illustrates an exemplary list of answers supplied by a subject individual in response to a plurality of queries relating to the subject individual's exhibition of some characteristics. The queries may be generated using a dynamic surveying method described later. The query answers could be received in electronic form or the query answers may be received in paper form.

As illustrated at step 106 in the flow chart of FIG. 1, the diagnostic method may further involve processing the received information (from step 104) and/or the accessed data (from step 102). The processing may be performed in any known manner compatible with the present invention. For example, the processing may be performed according to one or more algorithms, and/or the processing might involve use of an artificial intelligence engine.

Processing in step 106 may generate a diagnosis reflecting a sample's predisposition to exhibit the second group of characteristics. For example, the diagnosis may be that an individual who exhibits a first group of characteristics (e.g., male gender, not concerned about hair loss, concerned about white hair, not concerned about dandruff, no smoking habit, not concerned about baldness, fine hair, and red hair) is likely to have previously exhibited in the past, to be exhibiting at the present time, and/or will be exhibiting in the future a second group of characteristics (e.g., hair loss and often use of a fingernail multivitamin treatment). Such a diagnosis may be presented to the individual, to a health care professional, beauty care professional or any other individual or entity.

Based on the diagnosis, one exemplary method may provide a prompt for a further diagnostic examination of a subject individual by a practitioner. Examples of practitioners may include a health care provider, beauty consultant, beauty care provider, dietician, medical care provider, etc.

Alternatively (or additionally), the method may provide a prompt for an individual to alter some habit, lifestyle, personal care, etc. In another alternative (or additional) feature, the method may include informing the subject about at least one product for use by the subject. The product may be chosen from beauty products, health products, and medical products. Further, the product may be offered for sale to the subject. If the diagnosis reflects a predisposition for the subject to exhibit a condition (e.g., cosmetic condition, health condition, medical condition, etc.), then the product may include a product for treating the condition.

The term "product", as used herein, generically refers to tangible merchandise, goods, services, and actions performed. The term "beauty product" includes any product used for beauty, any beauty care product, any cosmetic product, and any similar product. A beauty product may be a product as defined above for affecting one or more external body conditions, such as conditions of the skin, hair and/or nails. Examples of tangible merchandise forms of beauty products include cosmetic goods, such as treatment products, personal cleansing products, and makeup products, in any form (e.g., ointments, creams, gels, sprays, supplement, ingesta, inhalants, lotions, cakes, liquids, and powders.)

Examples of service forms of beauty products include hair styling, hair cutting, hair coloring, hair removal, skin treatment, make-up application, and any other offering for aesthetic enhancement. Examples of other actions performed include massages, facial rubs, deep cleansings, applications of beauty product, exercise, therapy, or any other action effecting the external body condition whether performed by a professional, the subject, or an acquaintance of the subject.

The following is exemplary and non-exhaustive listing of a few beauty products: scrubs, rinses, washes, moisturizers, wrinkle removers, exfoliates, toners, cleansers, conditioners, shampoos, cuticle creams, oils, and antifungal substances, anti-aging products, anti-wrinkle products, anti-freckle products, skin conditioners, skin toners, skin coloring agents, tanners, bronzers, skin lighteners, hair coloring, hair cleansing, hair styling, elasticity enhancing products, agents, blushes, mascaras, eyeliners, lip liners, lipsticks, lip glosses, eyebrow liners, eye shadows, nail polishes, foundations, concealers, dental whitening products, cellulite reduction products, hair straighteners and curlers, and weight reduction products.

"Advice" includes one or more of product recommendations (e.g., product recommendations for products to treat conditions), remedial measures, preventative measures, predictions, prognoses, price and availability information, application and use information, suggestions for complementary products, lifestyle or dietary recommendations, or any other information intended to aid a subject in a course of future conduct, to aid a subject in understanding past occurrences, to reflect information about some future occurrences related to the subject or to aid a subject in understanding one or more products, as defined above.

One example of the method illustrated in the flow chart of FIG. 1 may involve accessing data from a database of individuals' characteristics, wherein there may be links between groups in the characteristics. Information about characteristics of a subject individual may be received by obtaining the subject individual's answers to a series of questions about the subject, such as those illustrated in FIG. 3A. The answers may represent information known by the subject. For example, the answers may indicate the subject, hypothetically named Durant Laurent, does not smoke, has fine, red hair, is male, is not concerned about hair loss, dandruff, or baldness, and is concerned about white hair. Processing of the accessed data and the received information may cause a diagnosis to be generated (and optionally presented to the subject and/or someone else), wherein the diagnosis may include one or more characteristics known by the subject (e.g., characteristics the subject is actually aware of and/or characteristics the subject could become aware of readily without undergoing any sophisticated analysis), but not previously provided by the subject. For example, the diagnosis may indicate that Durant Laurent exhibits the characteristics illustrated in FIG. 3B, even though none of those characteristics was provided in the answers of FIG. 3A.

In addition to (or rather than) generating a diagnosis including one or more characteristics "known" by the subject, the diagnosis may include one or more characteristics not "known" by the subject (e.g., characteristics that the subject could not become aware of without undergoing a relatively sophisticated analysis). For example, the diagnosis may also indicate that Durant Laurent has a cholesterol level between 493 to 743 millimoles per liter, tryglyceride level between 0.62 and 2.47, glycemia level greater than 61.0 millimoles per liter, iron level greater than 90, mean systolic arterial pressure level in the year 1996 (M_tas96) greater than 123.6, mean dystolic arterial pressure level (M_tad) of 79.6, above average anxiety score, and above average depression, as illustrated in FIG. 3C, even though Mr. Laurent did not "know" those characteristics. Note that the diagnosis of FIG. 3B and/or FIG. 3C contains relatively large amounts of somewhat specific information derived from a relatively small amount of somewhat general data provided by Mr. Laurent in FIG. 3A.

In another example, another subject, hypothetically named Yolanda Lauex, may provide answers to questions, as illustrated in FIG. 3D, in a manner similar to that described above for Durant Laurent. From the information provided in the answers, Yolanda Lauex may be diagnosed with characteristics illustrated in FIGS. 3E and 3F. FIG. 3E illustrates characteristics "known" and not provided by Yolanda. FIG. 3F illustrates characteristics not "known" and not provided by Yolanda. Again, note that the diagnosis in FIG. 3E and/or FIG. 3F contains a relatively large amount of somewhat specific information derived from a relatively small amount of somewhat general data provided by Yolanda in FIG. 3D.

As mentioned above, the data accessed in step 102 of FIG. 1 may be data organized by an artificial intelligence engine. "Artificial intelligence" (AI) is used herein to broadly describe any computationally intelligent system that combines knowledge, techniques, and methodologies. An AI engine may be any system that is configured to apply knowledge and that can adapt itself and learn to do better in changing environments. Thus, the AI engine may employ any one or combination of the following computational techniques: neural network (e.g., Kohonen map, multi-layer perceptron, etc.), constraint program, fuzzy logic, classification, conventional artificial intelligence, symbolic manipulation, fuzzy set theory, evolutionary computation, cybernetics, data mining, approximate reasoning, derivative-free optimization, decision trees, or soft computing. Employing any computationally intelligent technique, the AI engine may learn to adapt to unknown or changing environment for better performance. AI engines may be implemented or provided with a wide variety of components or systems, including one or more of the following: central processing units, co-processors, memories, registers, or other data processing devices and subsystems.

The AI engine may be trained based on input such as characteristic information, expert advice, user profile, or data based on sensory perceptions. Using the input, the AI engine may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, or recording learning. As a result of the training, the AI engine may learn to modify its behavior in response to its environment, and obtain knowledge. Knowledge may represent any information upon which the AI engine may determine an appropriate response to new data or situations. Knowledge may represent, for example, relationship information between two or more characteristics. Knowledge may be stored in any form at any convenient location, such as a database.

In another method in accordance with features and principles of the present invention, an AI engine, such as that described above, may be used to generate a profile data set from accessed data. The profile data set may be used to generate links from the accessed data. Or the generated profile data set may contain the links. For example, a large quantity of data may be accessed as described above (step 102) and processed using an AI engine to organize the data. The AI engine may be configured to organize the data based on a predetermined group of characteristics. The group of characteristics may be predetermined by the AI engine, an expert, algorithm, or other mechanism. Links may be drawn from the organized data or the organized data may contain links as described below.

Figure 4:
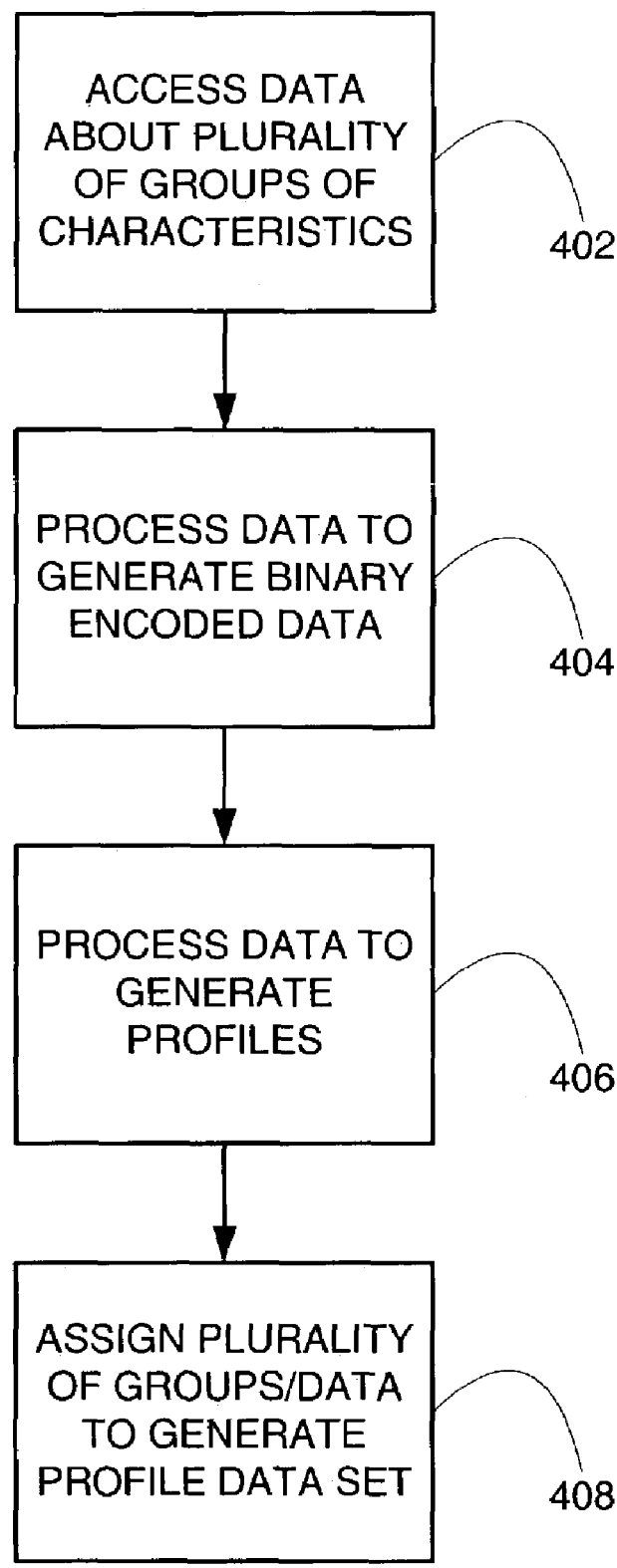
FIG. 4 illustrates an exemplary flow chart for a method of generating a profile data set consistent with features and principles of the present invention.

Consistent with features and principles of the invention, the method may include accessing data about a plurality of groups of characteristics, as illustrated at step 402 in the flow chart of FIG. 4. Accessing may be performed via any of mechanisms described above for step 102 in FIG. 1.

Also consistent with the invention, the method may include processing the accessed data, using an artificial intelligence engine, to generate binary encoded data representing modalities of the characteristics, as illustrated at step 404 in the flow chart of FIG. 4. A characteristic may contain qualitative information. Qualitative information (i.e., qualitative data) may include any information relating to or concerning one or more qualities. The modalities of the characteristic may be qualitative ordinal variables of the characteristic. For example, many characteristics are by definition limited to a finite number of values (so-called discrete variables) that may be qualitative. Take, for example, the characteristic of marital status, which may be single, widow, divorced, married, or separated. This kind of characteristic is referred to as a nominal qualitative variable, and the different possibilities of the characteristic called modalities. When a characteristic only has two modalities, it is referred to as a binary characteristic. For instance, a certain characteristic may be present or absent in an individual, (e.g., whether the individual has ever worn an earring) thus the characteristic is a binary characteristic. In accordance with step 404 of FIG. 4, regardless of the number of modalities associated with a characteristic, the characteristic may be encoded into a binary form suitable for processing using an artificial intelligence engine.

Forms of binary encoding may include unconstrained binary encoding, additive binary encoding, disjunctive binary encoding, and/or any other encoding consistent and compatible with features and principles of the invention. Unconstrained binary encoding may be used for characteristics with two modalities. In general, these characteristics may be encoded with values of 0 or 1. For example, the gender characteristic may have only two modalities, so the first modality (e.g., male) may be encoded as 1 and the second modality (e.g., female) may be encoded as 0.

FIG. 5 illustrates an exemplary table of modalities using additive binary encoding for a characteristic on the frequency of usage of a temporary hair color treatment, for example. As illustrated at question forty-three in the survey of FIG. 2, the characteristic may have three modalities (rare, often, not at all). The characteristic may be binary encoded as indicated in the exemplary table of FIG. 5. For example, if an individual filling out the survey indicates often usage of the treatment, then the corresponding modality two, may be binary encoded to 110. Such a table may be extended or shortened for characteristics with different number of modalities. For example, a characteristic with N modalities may be encoded into a binary code with N binary digits. If a characteristic exhibits the qualitative information associated with the $I^{th}$ modality, then the first to $I^{th}$ binary digits may be 1 and the $(I+1)^{th}$ to $N^{th}$ binary digits may be 0.

FIG. 6 illustrates an exemplary table of modalities using disjunctive binary encoding. The table has four modalities with their corresponding binary encoding. Again, the table may be extended or shortened for characteristics with different number of modalities. For example, a characteristic with N modalities may be encoded into a binary code with N binary digits. If a characteristic exhibits the qualitative information associated with the $I^{th}$ modality, then the all the binary digits except for the $I^{th}$ binary digit may be 0 and the $I^{th}$ binary digit may be 1.

A group of characteristics with their corresponding modalities may be encoded using one or a combination of binary encoding routines. FIGS. 7A and 7B show an example of how a group of characteristics may be encoded using a combination of encoding routines. FIG. 7A shows an exemplary table with a group of characteristics and their corresponding modalities. Gender, concern about hair loss, concern about white hair, concern about dandruff, concern about baldness, and smoke characteristics have modalities encoded using unconstrained binary encoding. Hair coarseness and natural hair color characteristics have modalities encoded using disjunctive and additive binary encoding, respectively. Using the information shown in FIG. 7A, FIG. 7B shows an example of a group of characteristics in the form of binary encoded data 704 for a person, hypothetically named John, who is male, not concerned about hair loss, dandruff, or baldness, concerned about white hair, does not have a smoking habit, and has fine, red hair characteristics. Labels 702 in FIGS. 7A and 7B illustrate which of the binary digits in the binary encoded data 704 correspond to which characteristic. Thus, label 'a' indicates the first binary digit in the binary encoded data 704 is the encoded gender characteristic; label 'b' indicates the second binary digit in the binary encoded data 704 is the encoded concern about hair loss characteristic; and the remaining labels indicate which remaining characteristics correspond to the remaining binary digits.

For purposes of the present invention, binary encoding may be performed in any feasible format and is not necessarily restricted to the examples described above. For example, the number of binary digits and the encoding scheme may be modified based on system design or requirements.

Figure 7C:
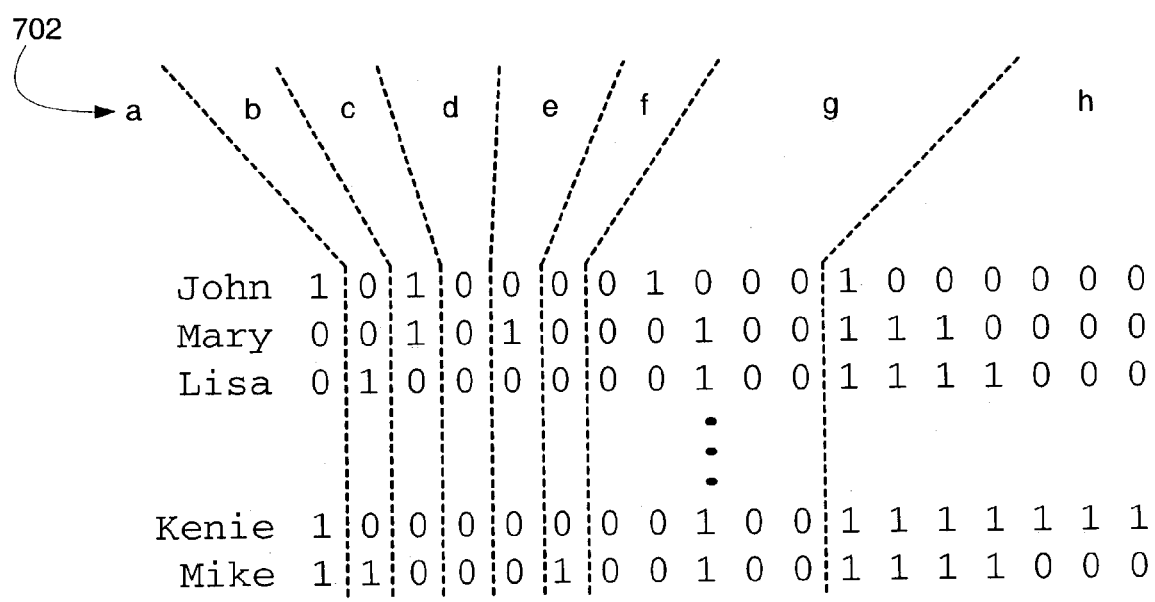
FIG. 7C illustrates exemplary binary encoded data of a plurality of individuals consistent with features and principles of the present invention.

The data accessed in step 402 of FIG. 4 may comprise characteristics of a plurality of individuals. For example, in addition to John in the above example, the binary encoded data 704 generated at step 404 in FIG. 4 may include encoded information for a plurality of individuals, hypothetically named John, Mary, Lisa, . . . , Kenie, and Mike, as illustrated in FIG. 7C.

According to features and principles consistent with the invention, the method may include processing the binary encoded data, using an artificial intelligence engine, to generate profiles for a profile data set, as illustrated at step 406 in the flow chart of FIG. 4. The artificial intelligence engine may generate a virtual grid 800 representing a profile data set of profiles as illustrated in an exemplary manner in FIG. 8. The grid 800 may comprise profiles 802 and connections 804 linking adjacent pairs of profiles 802. The connections 804 may be used to determine distance (e.g., proximity) between profiles 802. A distance of "one" between two profiles may be defined to be when the two profiles have a path with a single connection between them. A distance of "two" between two profiles may be defined to be when any path of connections between the two profiles has a minimum number of two connections. In a similar manner, a distance of M between two profiles may be defined to be when any path between the two profiles has a minimum number of M connections. The connections 804 may be used to define a set of profiles within a certain proximity of a particular, individual profile. For example, the connections 804 may be used to specify a neighborhood of a particular profile such as profile 806. A neighborhood of "one" for profile 806 would comprise a set of all profiles within one connection of profile 806. For example, all profiles in dotted box 808 are in the neighborhood of "one" for profile 806. All profiles in dotted box 810 are in a neighborhood of "two" for profile 806. Analogous neighborhoods exist for the other profiles. All or some information associated with profiles in a neighborhood may be referred to as neighborhood data.

Configurations of profiles are not limited to two-dimensional spaces (e.g., Cartesian plane). The profiles may be arranged in one-dimensional space, three-dimensional space, four-dimensional space, etc. Also, the neighborhood of a profile may be defined using distances besides the Euclidean distance, such as Hamming distance or any other metric known in the art and compatible with the present invention.

Figure 9:
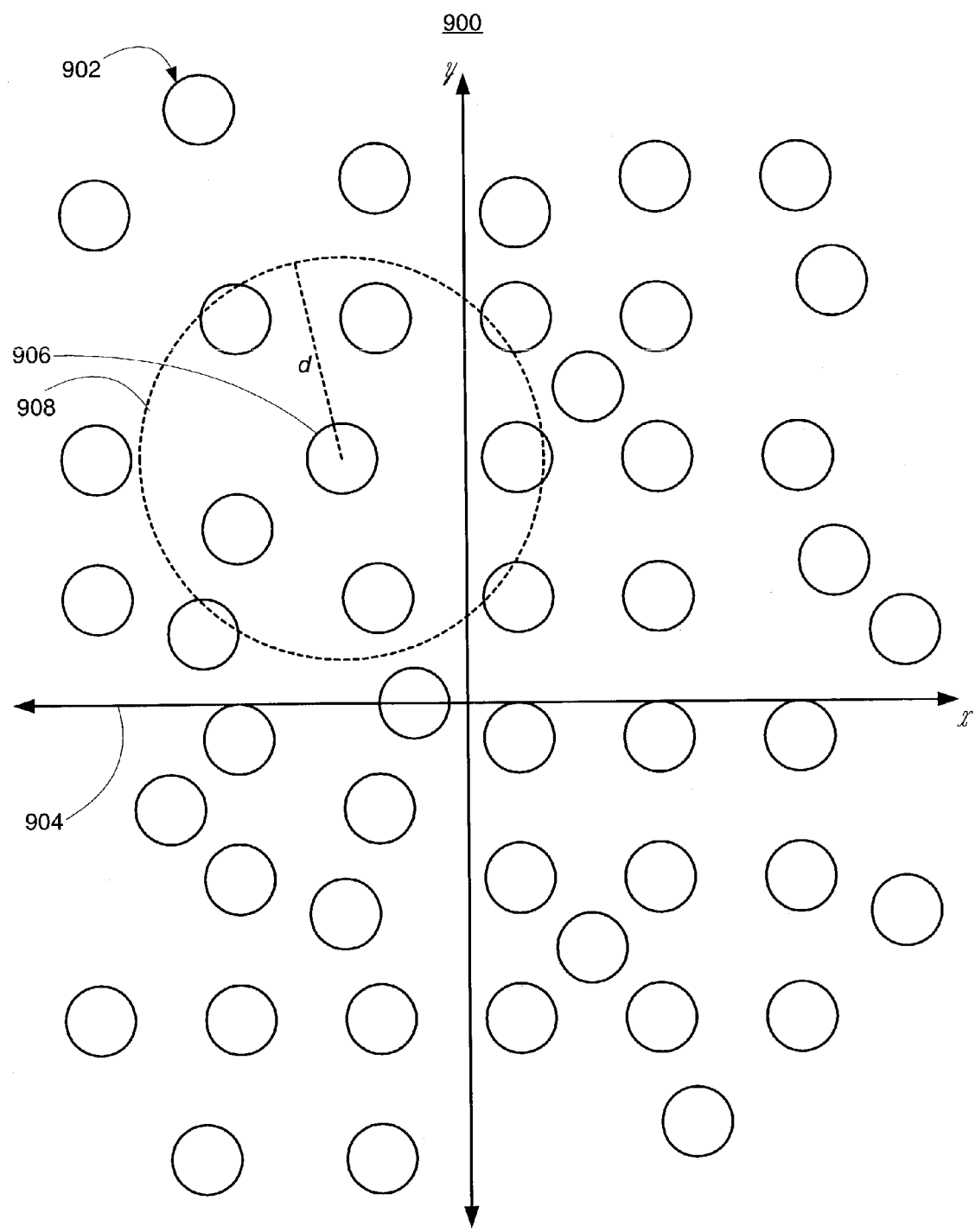
FIG. 9 illustrates an exemplary arrangement of profiles consistent with features and principles of the present invention.

Any number of profiles may be in a profile data set. The profiles may be arranged in any configuration compatible with the invention. Further, the neighborhoods of the profiles may be defined in any way compatible with the invention. For example, FIG. 9 illustrates an exemplary arrangement 900 of profiles wherein the profiles 902 are situated on a Cartesian plane 904 with corresponding locations defined by Cartesian coordinates. The Cartesian coordinates of a profile in this example are defined to be the coordinates of the center of the profile. In this arrangement 900, a neighborhood of a profile may be defined to be all profiles whose Cartesian coordinates are within a given Euclidean distance, d, of the profile's Cartesian coordinates. For example, all profiles with Cartesian coordinates within the dotted circle 908 of radius d are within the neighborhood of d of profile 906.

All profiles may contain a referent. The referent may be a binary code and may define the characteristics for its respective profile using any of the binary encoding methods previously described. For example, the referent for profile 806 in FIG. 8 may be 101000010001000000 (the example represented in FIG. 7b). According to the exemplary table in FIG. 7A, this referent would indicate a profile with male gender, unconcerned about hair loss, concerned about white hair, unconcerned about dandruff, unconcerned about baldness, no smoking habit, and fine, red hair. The referent for each profile may be determined during the processing step 406 of FIG. 4. This may involve using a neural clustering algorithm such as a dynamic cluster method, a k-means clustering algorithm, a hierarchical clustering algorithm, a mobile center method, and/or a topology map method. (Other algorithms may also be used.) As described in more detail later, the neural clustering algorithm may use neighborhood data.

Neural clustering algorithms may include methods described by Thiria, S., Lechevallier, Y., Gascuel O., and Canu, S. in *Statistique et methodes neuronales*, Dunod, Paris, 1997, which is incorporated herein by reference in its entirety.

A dynamic cluster method may begin by initializing the referent for each profile. The referent may be initialized randomly, pseudo-randomly, using an algorithm, and/or using any technique compatible with the invention. After initialization, the referent may be trained using binary encoded data representing characteristics from a plurality of groups. In the above example, FIG. 7C illustrates a plurality of binary encoded data for a plurality of respective individuals. Each one of the plurality of binary encoded data may be assigned to a profile with the closest matching referent. The profile with the closest matching referent may be determined using a metric that compares a degree the referent matches the binary encoded data of an individual. One metric, known as the hamming distance, inter alia, may be defined as $$d(z_i, p) = \sum_{j=1}^{B} |z_i(j) - r_p(j)|,$$

wherein $d(z_i, p)$ is the degree the referent $r_p$ of profile p matches the binary encoded data $z_i$ of the $i^{th}$ individual, $z_i(j)$ is the $j^{th}$ binary digit in $z_i$, $r_p(j)$ is the $j^{th}$ binary digit in $r_p$, and B is the number of binary digits in the binary encoded data. For this metric, a degree of lower value indicates a closer match. For example, the degree of match between binary encoded data 101000010001000000 and referent 101100010000100000 would be three and the degree of match between binary encoded data 101100010000100000 and referent 101100010000100000 would be zero. Binary encoded data that matches the referents of more than one profile with equal degree may be arbitrarily assigned to one of the profiles. A profile may have more than one binary encoded data assigned to it.

Figure 8:
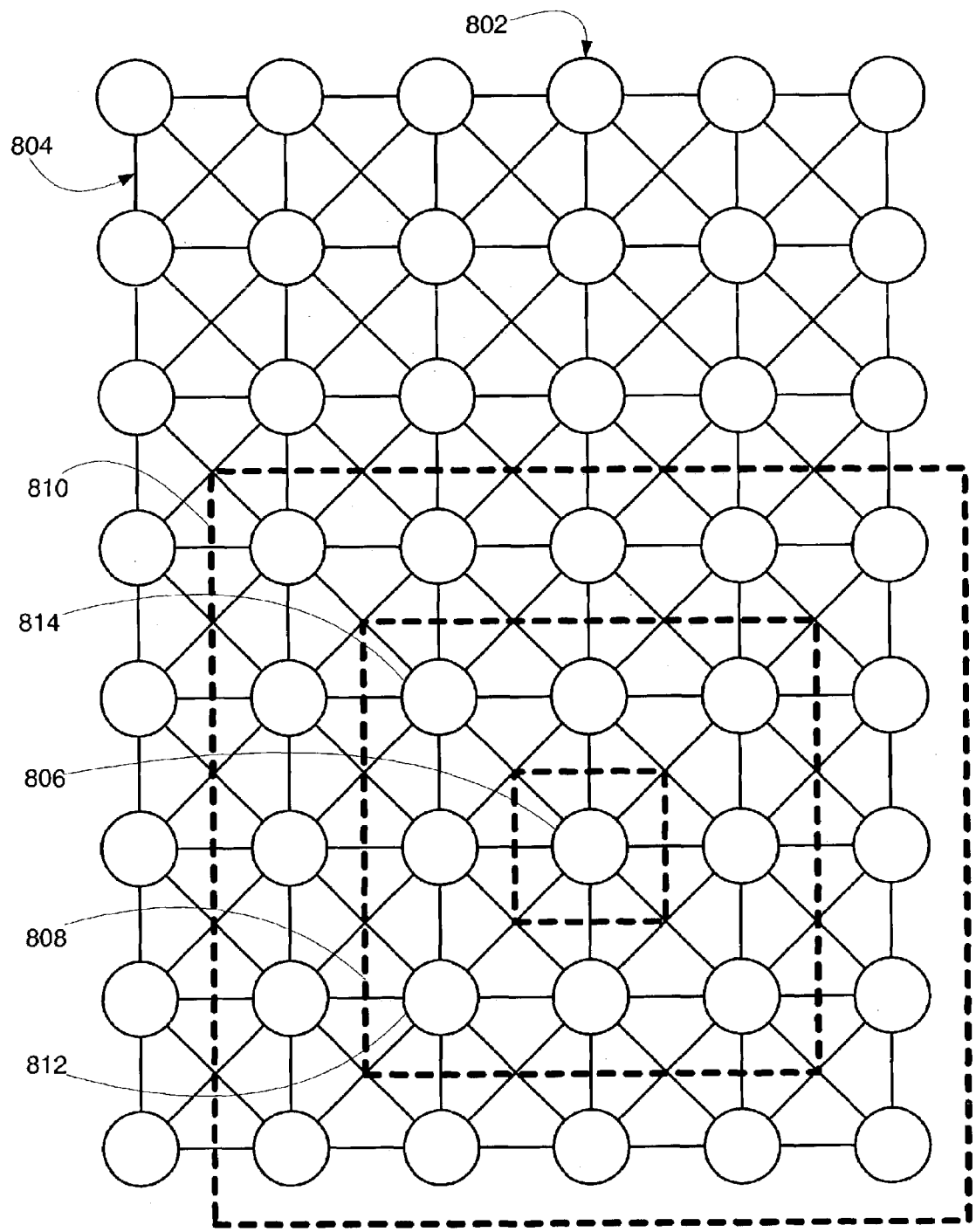
FIG. 8 illustrates an exemplary grid of profiles consistent with features and principles of the present invention.

Once all the binary encoded data from the plurality of individuals are assigned to a profile, the referent of each profile may be optimized. Optimization for the referent of a given profile may be performed by calculating a center median of all the binary encoded data assigned to profiles within a neighborhood of the given profile and then replacing the referent of the given profile with the center median. More particularly, the referent for the given profile may be optimized by $$r_c(j) = \underset{z_i \in N_c}{\text{median}}(z_i(j)),$$

wherein $r_c(j)$ is the $j^{th}$ binary digit of the optimized referent $r_c$ for the given profile c, and $N_c$ is the set containing all binary encoded data $z_i$ assigned to profiles within a neighborhood of the given profile c. In the above example, if profile 806 in FIG. 8 is assigned binary encoded data $z_5$ and $z_7$, profile 812 is assigned binary encoded data $z_4$ and $z_{13}$, and profile 814 is assigned binary encoded data $z_6$, $z_{10}$, and $z_{21}$, then the optimized referent r for profile 806 using binary encoded data within a neighborhood of one may be determined as illustrated in the table of FIG. 10. The $j^{th}$ binary digit of the referent r in profile 806 is the median of the $j^{th}$ binary digit of all the binary encoded data in the neighborhood (i.e. $z_4$, $z_5$, $z_6$, $z_7$, $z_{10}$, $z_{13}$, and $z_{21}$).

Figure 11:
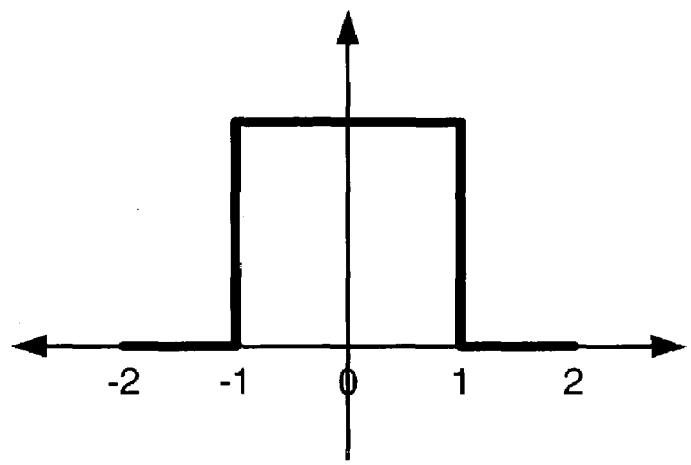
FIG. 11 illustrates an exemplary indicator function consistent with features and principles of the present invention.
Figure 12:
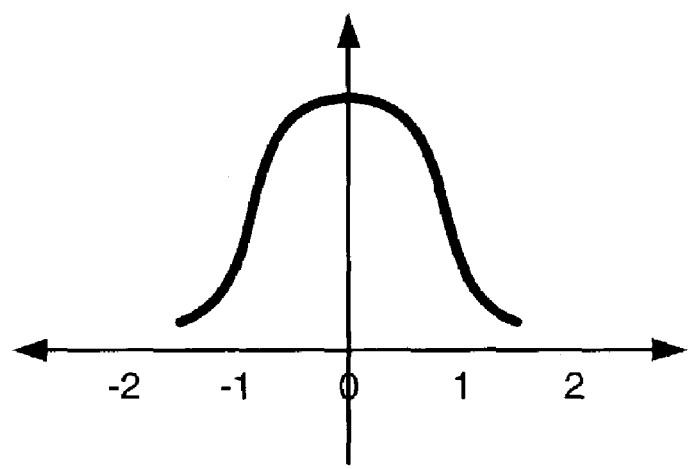
FIG. 12 illustrates an exemplary Gaussian function consistent with features and principles of the present invention.

In optimizing the referent of a given profile, the binary encoded data may be weighted as function of the proximity between the given profile and the profile to which the binary encoded data are assigned. FIG. 10 illustrates a center median calculated using uniform weighting because the binary encoded data used to determine the center median were all weighted with one. However, the center median in FIG. 10 was only calculated using binary encoded data from profiles within a neighborhood of one, so binary encoded data from profiles outside the neighborhood of one may be viewed as having a weight of zero. This may be characterized by the indicator function in FIG. 11, wherein the x-axis represents the distance of a neighboring profile from the given profile and the y-axis represents the weight applied to the binary encoded data in the neighboring profile. Other forms of weighting may include the Gaussian function illustrated in FIG. 12 or any other function compatible with features and principles of the present invention. Example of other functions may include, but are not limited to, discrete functions, continuous functions, probabilistic functions, etc.

After optimizing the referents of all the profiles, the binary encoded data in the profiles may be re-assigned to the profiles with the closest matching optimized referent. Referents of all the profiles may be optimized again using the re-assigned binary encoded data in the manner described above. The assignment of the binary encoded data and optimization of the referents may be repeated for a predetermined number iterations or until the referents converge (i.e., no longer change from one iteration to the next). The weighting applied to the binary encoded data during optimization may change for each iteration. For example, the weighting may decrease the number of binary encoded data used to optimize a referent by assigning a weight of zero to profiles beyond a certain distance from the profile having its referent optimized and decreasing the distance at each iteration. Decreasing this distance effectively shrinks the neighborhood of profiles used to optimize a referent.

Figure 13:
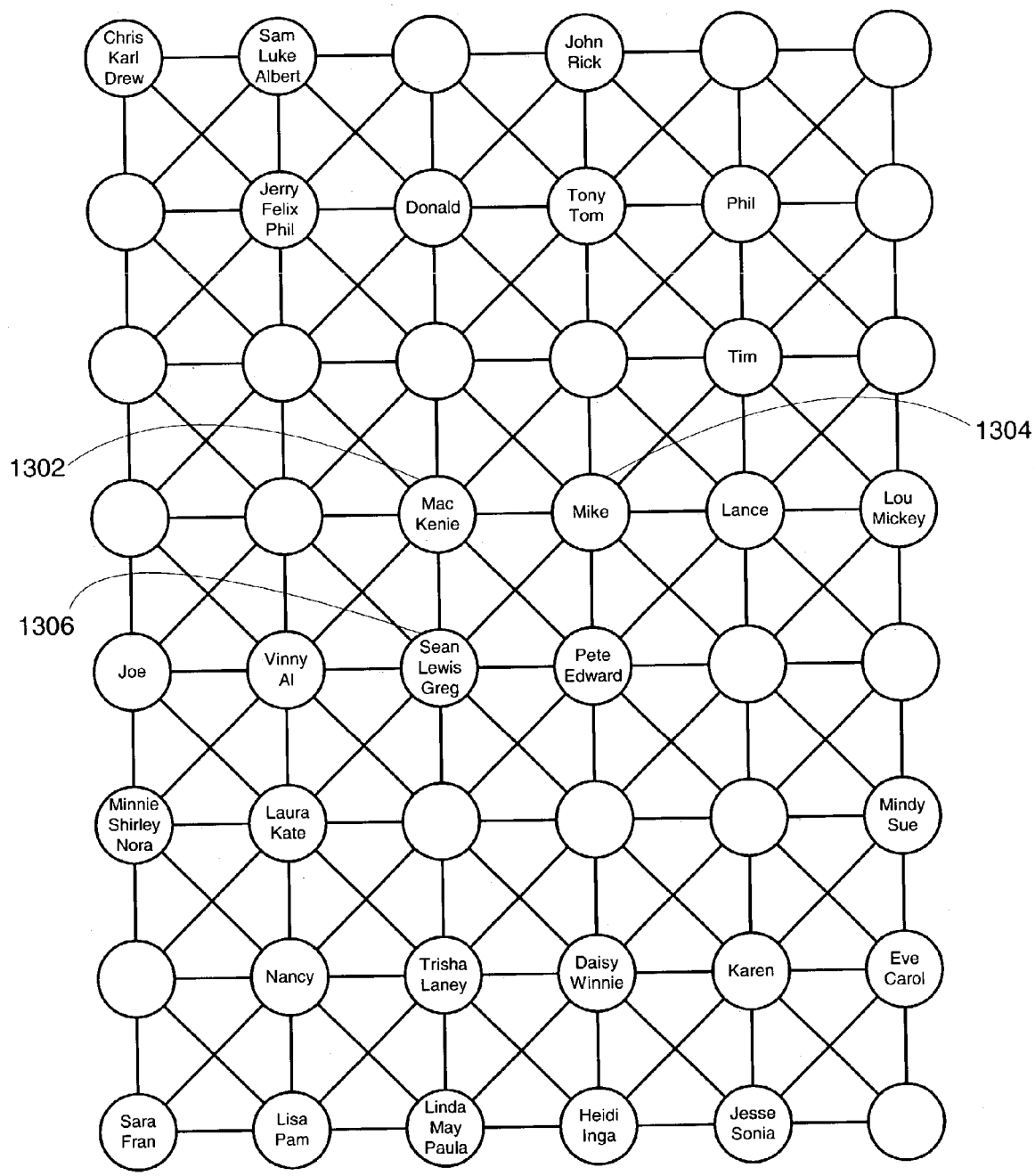
FIG. 13 illustrates an exemplary grid of profiles with assigned binary encoded data consistent with features and principles of the present invention.

The dynamic cluster method is finished once the assignment of binary encoded data and optimization of the referents are complete. FIG. 13 illustrates an example where the binary encoded data for individuals may be assigned in grid 800 of FIG. 8 after the dynamic cluster method is completed. For example, profile 1302 in grid 1300 has the binary encoded data of Mac and Kenie assigned to it because the profile 1302 contains the referent with the closest match to their binary encoded data. Further, profiles that are within proximity of each other may contain referents that are similar to each other because neighborhoods are used with the dynamic cluster method in optimizing referents. Therefore, profiles 1304 and 1306 may contain referents similar to the referent in profile 1302 and all the binary encoded data (i.e., Mike, Sean, Lewis, Greg) assigned to profiles 1304 and 1306 may be similar to the binary encoded data (i.e., Mac and Kenie) assigned to profile 1302. As a result, Mac and. Kenie may have characteristics similar to characteristics exhibited by Mike, Sean, Lewis, and Greg.

The above description of dynamic clustering may use the center median and/or Hamming distance for determining and optimizing the referent of each profile. Alternatively, the mobile center method may also be used for the same purpose. Instead of the center median and/or Hamming distance, the mobile center method may use a center of gravity (i.e., center mean) and/or Euclidean distance.

The above description for generating the clustered profiles in FIG. 13 uses a dynamic cluster method, but other methods compatible with the present invention may also be used. For instance, a k-means clustering algorithm may be used instead or in combination with the dynamic cluster method. Unlike the dynamic cluster method, which may optimize the referent of each profile when all the binary encoded data are assigned to the profiles, the k-means clustering algorithm may optimize the referent of a profile when less than all the binary encoded data have been assigned to the profiles. The k-means clustering algorithm may optimize the referent of each profile after each assignment of binary encoded data to a given profile. In the k-means clustering algorithm, the selection of at least one binary encoded data to be re-assigned may be performed randomly, pseudo-randomly, or using a prescribed method.

For example, at least one, but not all, of the binary encoded data assigned to the profiles may be selected and re-assigned to the profiles. After re-assigning, the referents of all of the profiles may be optimized. The referents may be optimized by calculating the center median of the binary encoded data in each profile. The assignment of at least one, but not necessarily all of, the binary encoded data and optimization of the referents may be repeated for a predetermined number iterations or until the referents converge (i.e. no longer change from one iteration to the next).

Alternatively, the optimization of the referents may use the dynamic cluster method at one iteration and the k-means clustering algorithm at another iteration. For example, at one iteration all the binary encoded data may be re-assigned and then the referents may be optimized. At another iteration, at least one, but not necessarily all of, the binary encoded data may be re-assigned and then some or all the referents may be optimized.

A hierarchical clustering algorithm may be applied to the dynamic clustered profiles in FIG. 13 (or k-means-clustered profiles or combined dynamic clustered and k-means-clustered profiles). The hierarchical clustering algorithm may reduce the number of profiles in grid 1300 by agglomerating the profiles in grid 1300. The first profile may be merged with a second profile, wherein a clustering index indicates the referent of the first profile matches closer to the referent of the second profile than a referent in any other profile in grid 1300. The clustering index may be a Ward index, pseudo-Ward index, a distance index, an index taking total number of binary encoded data, or any other index.

The Ward index is defined to be $$\Delta_{Ward} = \frac{n_a n_b}{n_a + n_b} \sum_{j=1}^{B} |r_a(j) - r_b(j)|,$$

wherein $n_a$ is the number of binary encoded data assigned to profile a, $n_b$ is the number of binary encoded data assigned to profile b, $r_a$ is the referent of profile a, $r_b$ is the referent of profile b, B is the number of binary digits in the referent, $r_a(j)$ is the $j^{th}$ binary digit in referent $r_a$, and $r_b(j)$ is the $j^{th}$ binary digit in referent $r_b$. For example, the referents of profiles 1302 and 1304 in FIG. 13 may be 1000000010011111111 and 1000000100011111110, respectively $r_a$ and $r_b$. The numbers of binary encode data in profiles 1302 and 1304 are two and one, respectively $n_a$ and $n_b$. Therefore, the Ward index between the two profiles is calculated to be two.

The pseudo-Ward index is defined to be $$\Delta_{Pseudo}(P_a, P_b) = \Phi(P_a \cup P_b) - \Phi(P_a) - \Phi(P_b),$$

wherein $P_a$ and $P_b$ are sets of binary encoded data contained in the profiles a and b, respectively, and $\Phi(S)$ is the inertia of a given set S. For example, $\Phi(P_a)$ is defined to be $$\Phi(P_a) = \sum_{i=1}^{n_a} \sum_{j=1}^{B} |z_{a,i}(j) - r_a(j)|,$$

wherein $z_{a,i}$ is the $i^{th}$ binary encoded data in profile a, and $z_{a,i}(j)$ is the $j^{th}$ binary digit in $z_{a,i}$.

The distance index is defined to be $$\Delta_{Dist} = \sum_{j=1}^{B} |r_a(j) - r_b(j)|.$$

In the above example, the distance index between profiles 1302 and 1304 would be three.

The index taking total number of binary encoded data is defined to be $$\Delta_{Total}(P_a, P_b) = \frac{2\Phi(P_a \cup P_b)}{B(n_a + n_b)}.$$

The referent for the merged profile of two merging profiles may be set to the referent of the merging profile with more binary encoded data assigned to it. For example, if profiles 1302 and 1304 are merged, the referent of the merged profile may be the referent of profile 1304 because profile 1304 has more binary encoded data assigned to it than profile 1302. Alternatively, the referent of the merged profile may be set using any other criteria or algorithm compatible with the invention. Profiles in the grid may continue to be merged together until only a predetermined number of profiles remain, until the combined profiles contain a certain number of binary encoded data, or until any other criteria for final clustering is achieved.

Figure 14:
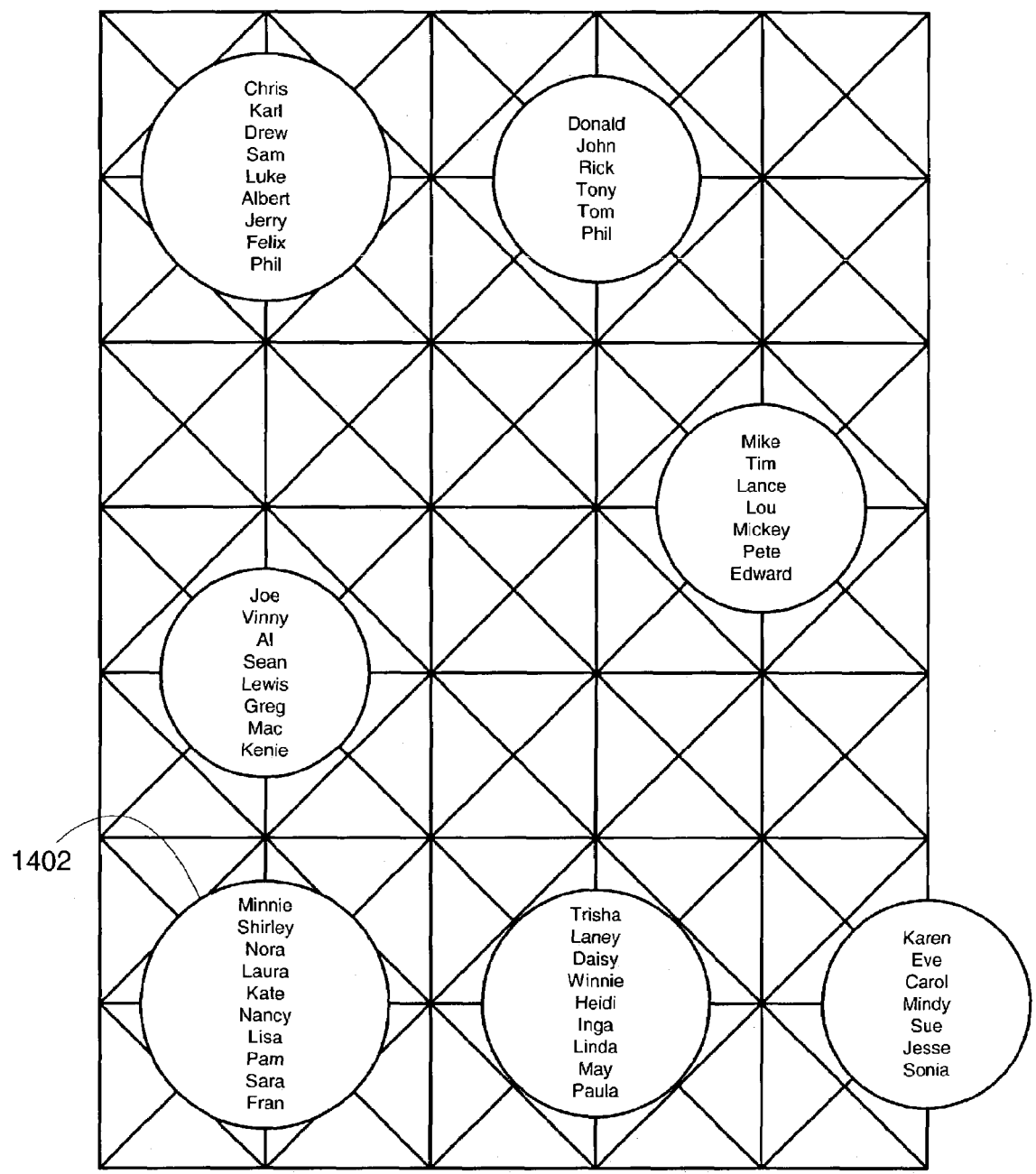
FIG. 14 illustrates exemplary merged profiles consistent with features and principles of the present invention.

After hierarchical clustering, an exemplary set of merged profiles may look like the example shown in FIG. 14. Since the clustering algorithm described above may organize individuals in the grid 1400 by placing individuals with similar binary encoded data in the same profile, the individuals in a given profile may have similar characteristics. Further, the referent of any profile may be binary data and can be decoded using the table in FIG. 7A to a corresponding referent group of characteristics. The referent group of characteristics of a profile may be substantially representative of the characteristics exhibited by individuals in the profile. For example, the referent of profile 1402 may be 0110010010011111100. Using FIG. 7A, the group of characteristics corresponding to the referent is female gender, concerned about hair loss, white hair, and baldness, not concerned about dandruff, smoking habit, and average, dark chestnut blonde hair. Therefore, all individuals in profile 1402 may substantially exhibit the characteristics of the referent group.

According to features and principles of the present invention, as illustrated at step 408 in the flow chart of FIG. 4, the method may include assigning at least some of the plurality of groups of characteristics, the accessed data, and/or the binary encoded data using the artificial intelligence engine, to the profiles to generate a profile data set. With reference to the example shown in FIG. 14 and as described above, the binary encoded data assigned to the profiles in the figure reflect a group of characteristics (e.g., gender, concern about hair loss, concern about white hair, concern about dandruff, concern about baldness, smoking habits, coarseness of hair, and color of hair) for a plurality of individuals. Additional groups of characteristics of the individuals not used to organize the individuals in grid 1400 may be assigned to the profiles containing the individual. For example, an additional group of characteristics of individuals in a profile, including characteristics such as whether there is occurrence of hair loss and usage of fingernail multivitamin treatment, may be assigned to the profile containing the respective individual. If the individuals in a profile substantially exhibit the same characteristics in the additional group of characteristics, then a link may be made between the characteristics reflected in the referent of the profile and the additional group of characteristics. However, a link may also be made within the characteristics reflected in a referent of the profile by virtue of the fact that the generation of the profiles at step 406 uses binary encoded data reflecting characteristics to generate the profiles.

For example, if individuals in profile 1402 in FIG. 14 substantially exhibit hair loss and frequent usage of fingernail multivitamin treatment, then a link may be made indicating a subject individual exhibiting characteristics reflected in the referent of profile 1402 has likely exhibited in the past, is likely exhibiting at the present time, or will likely exhibit in the future, hair loss and frequent usage of fingernail multivitamin treatment.

Once the profile data set is generated it may be updated. Additional data from other individuals may be collected to train the referents in the profile data set. The additional data may be added to previous characteristic data and processed as described above to generate a new profile data set.

With reference to FIG. 1 and FIG. 4, the diagnostic method as illustrated in the flow chart of FIG. 1 may use a profile data set, for example to diagnose a subject individual. In such an example, at step 102 in FIG. 1, the accessed data about the plurality of groups of characteristics may include a first group of characteristics from a plurality of individuals. The first group may comprise gender, concern about hair loss, concern about white hair, concern about dandruff, smoking habit, concern about baldness, coarseness of hair, and color of hair characteristics. At step 106 in FIG. 1, the group of characteristics from the plurality of individuals may be used to organize the individuals into a profile data set. The plurality of individuals may be assigned to profiles in the profile data set based on their respective characteristics from the first group or other characteristics in the plurality of characteristics. The individuals may be assigned to profiles according to how close their characteristics match the characteristics reflected in the referent of each profile.

Further, the received information at step 104 in FIG. 1 may reflect the exhibition of the first group of characteristics of a subject individual. The received information may be binary encoded or already binary encoded. The profile with the referent matching closest to the binary encoded data may contain individuals displaying characteristics substantially similar to the subject individual. The profile may also contain additional characteristics (e.g., a second group of characteristics) not used to organize the individuals in the profile data set. Therefore, the subject individual may be diagnosed to have a predisposition to exhibit the additional characteristics of the individuals in the profile.

A third embodiment of the invention may include a dynamic surveying method. According to features and principles of the present invention, the method may include accessing data organized by an AI engine as illustrated at step 1502 in the flow chart of FIG. 15. Accessing may be performed using mechanisms as previously described. For example, the accessed data may include personal information such as information identifying characteristics and information for predicting evolution of the identified characteristics. Information for predicting the evolution of the identified characteristics may include links derived using the artificial intelligence as previously described. The accessed data may include a profile data set generated as previously described.

Figure 15:
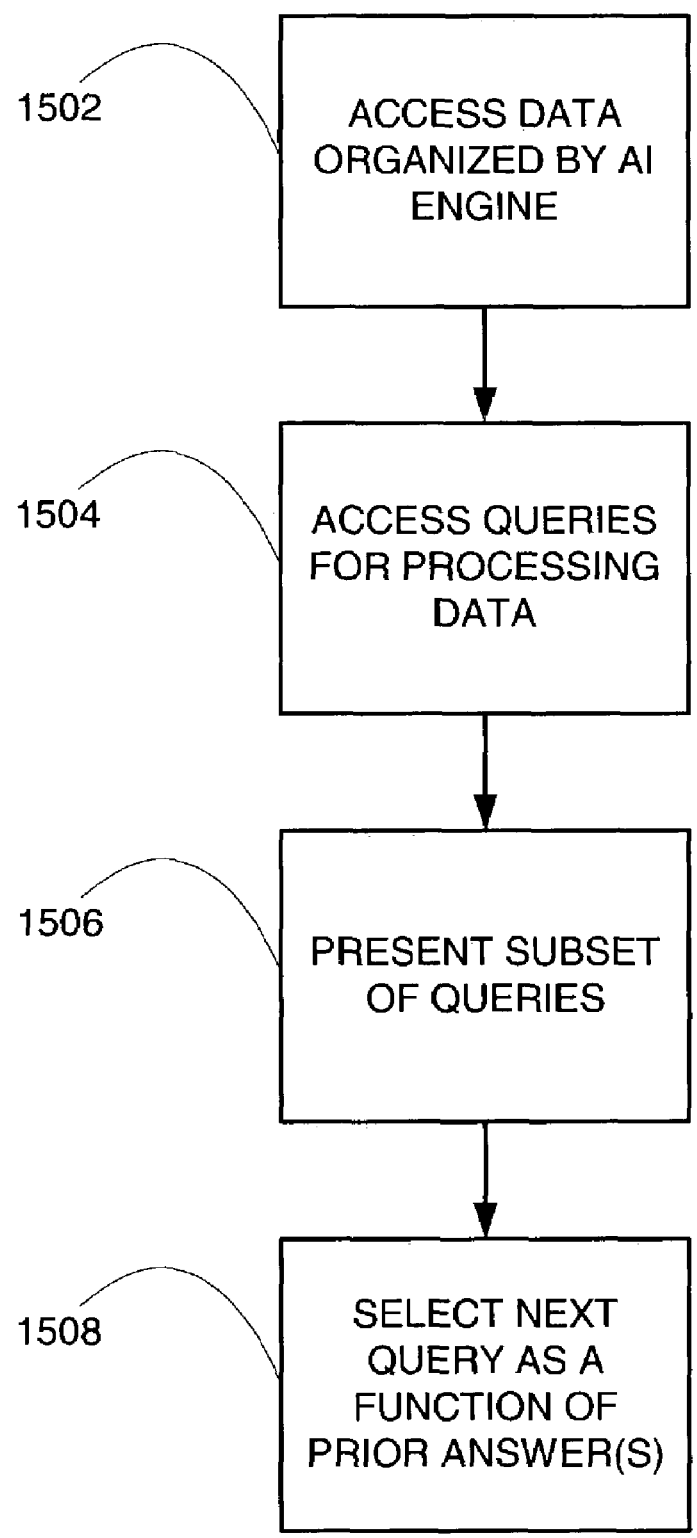
FIG. 15 illustrates an exemplary flow chart for a method of dynamic surveying.

Consistent with the present invention, the dynamic surveying method may include accessing queries and presenting to a subject a subset of queries from the accessed queries, as illustrated at steps 1504 and 1506 in the flow chart of FIG. 15. The accessed queries may be stored in some form using any storage medium described above or generated. The queries may include questions that elicit one or more answers that may be used to process at least some of the data accessed in step 1502. For example, one or more answers to the queries may reflect whether a group of characteristics are exhibited by the individual. Additionally (or alternatively), the group of characteristics may be different from the one or more characteristics being diagnosed and may be linked with the characteristics being diagnosed. Presenting of the query subset to the subject may include direct or indirect actions. Direct actions of presenting may include displaying queries on a video screen, orally posing the queries to the subject, providing a printed document containing the queries, etc. Indirect actions may include preparing queries for subsequent actions directly presenting the queries, such as sending queries to a third party to pose the queries to the subject, converting queries into digital form for presenting over a network, etc.

Consistent with the present invention, the dynamic survey method may include selecting, for at least some of the queries presented, a next query as a function of the subject's answer to a previous query, as illustrated at step 1508 in the flow chart of FIG. 15. The selecting could be performed using an algorithm, an artificial intelligence engine, and/or any other techniques. Selecting may include determining queries that elicit answers reflecting whether the subject exhibits a first group of characteristics. The queries may be selected to present the fewest number of queries to the subject before providing at least one of a diagnostic, advice, and/or information to the subject. Alternatively (or additionally), the queries may be selected linearly or sequentially until the subject's answers to the selected queries supply enough information to provide at least one of a diagnostic, advice, and/or information to the subject. A next query in a series of queries may be selected based on the answer to a previous query.

For example, one embodiment of the present invention may involve accessing a profile data set, such as one illustrated in FIG. 13 or 14. The profile data set may be generated using information from a survey (or other mechanism), such as the exemplary survey illustrated in FIG. 2, as previously described. Queries used to determine which characteristics are exhibited by a subject may be accessed and presented to the subject. The answers to the queries may be used to determine which profile in the profile data set best describes or is most suitable to the subject. For example, the queries may ask the subject whether the subject is a man or a woman, whether the subject is concerned about hair loss, white hair, or dandruff, whether the subject smokes, whether the subject has certain degrees of oiliness of hair, etc. A profile in the profile data set that most closely resembles answers provided by the subject may be selected. Additional information (e.g., Body Mass Index (BMI), blood characteristics, etc.) in the selected profile and not provided in the answers of the subject may be presented to the subject (or to another entity, such as a practitioner) as a diagnosis. In addition (or in the alternative), certain embodiments of the method may involve generating advice and/or information based on the processing of the accessed data.

In selecting the profile that most closely resembles answers provided by the subject, portions of the profile data set may be narrowed (e.g., reduced, excluded, etc.) until a suitable profile remains for presenting to the subject. Prior to finding a suitable remaining profile, the queries may also be used to indicate whether the subject resembles at least some characteristics and/or aspects in a particular profile in the profile data set. The queries may be selected to efficiently exclude portions of the profile data set. For example, if half of the profiles in a profile data set have male gender for a gender characteristic and half have female gender, and if a third of the profiles have oily hair, a third have non-oily hair, and a third have very oily hair, then a query asking whether the subject has non-oily, oily, or very oily hair would narrow a portion of the profile data set more efficiently than a query asking whether the subject is male or female. More particularly, once a subject answers a query about oiliness of hair, two-thirds of the profiles in the profile data set may be excluded because those profiles do not apply to the subject. Whereas, once a subject answers a query about gender, the profile data set is merely reduced by one-half. According to such an example, one embodiment of the method includes presenting a query relating to oiliness of hair before considering presenting a query relating to gender.

As one of ordinary skill in the art will appreciate, various algorithms (e.g., tree-searching algorithms, shortest-path algorithms, network algorithms, etc.) for selecting queries to efficiently exclude profiles of a profile data set based on the answers from the subject and characteristics contained in the profiles may be used with the present invention. Further, besides algorithms, various artificial intelligence engines, as described above, may be used to select the queries to efficiently reduce the profile data set.

Alternatively, the queries may be selected sequentially through a sequence of queries about characteristics in the profiles. For example, a list of queries asking the subject about gender, concern about hair loss, concern about white hair, concern about dandruff, smoking habits, etc. may be presented to the subject sequentially or in a prescribed order regardless of how efficient the queries and answers are in narrowing portions of the profile data set. Once the subject answers enough queries to identify a profile in the profile data set that best matches the characteristics exhibited by the subject, then no additional queries may need to be presented to the subject.

As mentioned above, whether the queries are selected efficiently or inefficiently, according to an exemplary embodiment at least one next query selected and presented to the subject may be based on at least one answer to a previous query. For instance, in the previous example, a profile data set may contain an equal number of profiles with non-oily, oily, and very oily hair characteristics. However, all the profiles with the non-oily hair characteristic may contain the concerned about dry hair characteristic, all the profiles with the oily hair characteristic may contain the not concerned about dry hair characteristic, half the profiles with the very oily hair characteristic may contain the concerned about dry hair characteristic and the remaining half of the profiles with the very oily hair characteristic may contain the not concerned about dry hair characteristic.

If the subject's answer to a previous query about oiliness of hair is that the subject exhibits the non-oily hair characteristic, then a next query may not ask about the subject's concern about dry hair characteristic because the answer to such a query either won't further narrow the reduced profile data set containing the oily hair characteristic or will completely exclude all profiles in the reduced profile data set containing the oily hair characteristic. Instead, the next query may be selected to more effectively narrow portions of the reduced profile data set containing the non-oily hair characteristic. If the subject's answer to a previous query about oiliness of hair is that the subject has very oily hair, then the next query may ask the subject whether the subject is concerned about dry hair.

Features and principles of the present invention may be implemented in a system comprising a data processor (or data processors) and a storage medium (or storage media). The data processor and storage medium may be functionally coupled. The storage medium may contain instructions to be executed by the data processor for performing methods consistent with the present invention. Data processors may include desktops, mainframes, computers, application specific integrated circuits, electronic devices, mechanical devices, and/or any other mechanism for executing instructions. The storage medium may include any storage media as previously described.

Figure 16:
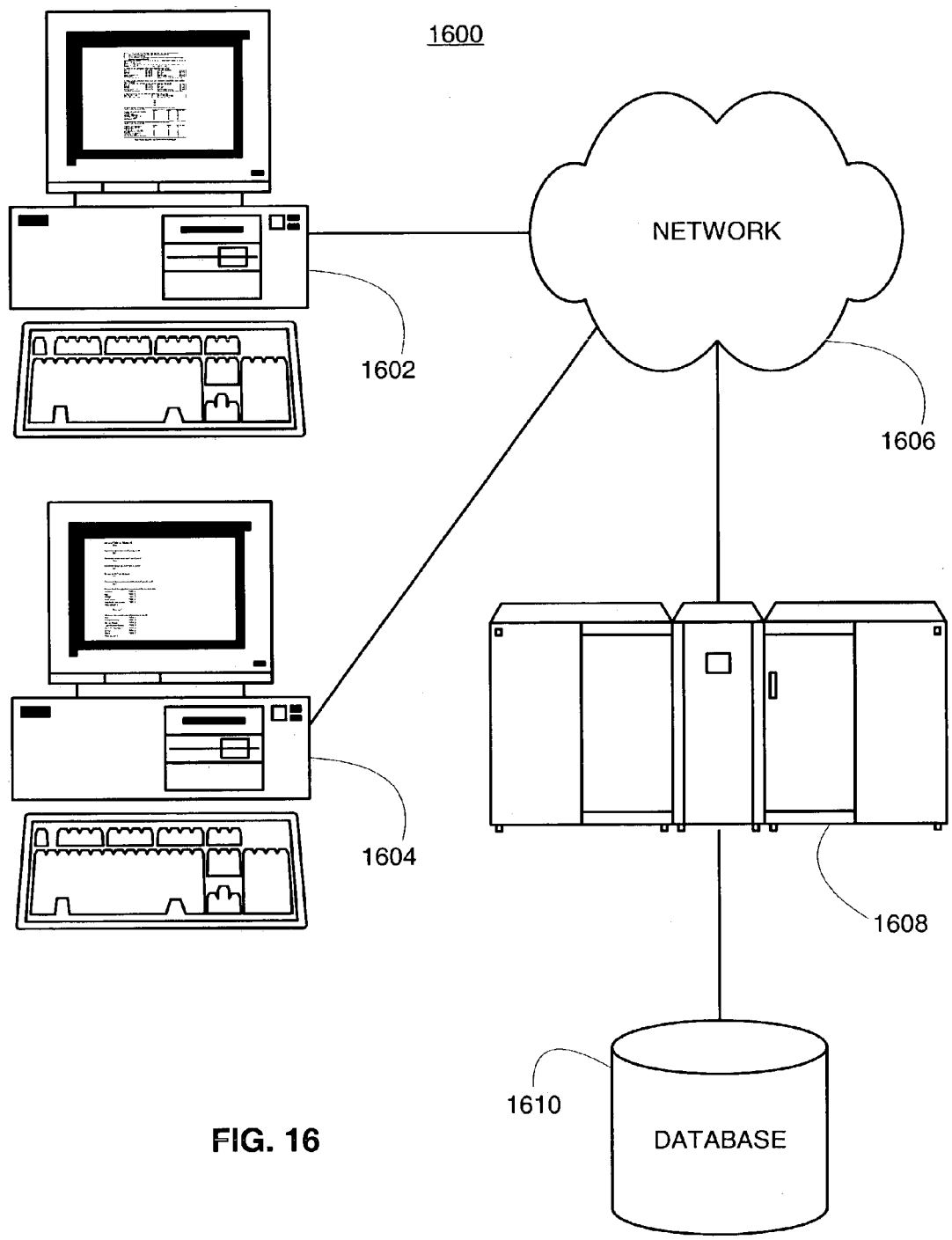
FIG. 16 illustrates an exemplary system implementing features and principles of the present invention.

For example, features and principles of the present invention may be implemented in system 1600 of FIG. 16. The system 1600 may comprise a computer kiosk 1602, a computer terminal 1604, a network 1606, a mainframe 1608, and a database 1610. A plurality of individuals may fill out a survey containing data about characteristics of the individuals at the computer kiosk 1602. The mainframe 1608 may access the data via the network 1606. A subject individual may send information via the network 1606, in response to a series of queries, reflecting that the subject exhibits some of the characteristics. The queries may be selected using the dynamic surveying method described above. The mainframe 1608 may receive the information and process the received information and accessed data to generate a diagnosis, advice, and/or any other information. The mainframe 1608 may be configured to generate a profile data set by accessing data, processing the accessed data to produce binary encoded data, processing the binary encoded data using an artificial intelligence engine to generate profiles, and assigning the characteristics to the profiles to generate the profile data set.

The computer kiosk 1602, computer terminal 1604, and mainframe 1608 may be any computing platform, including a stand-alone personal computer or networked computers. Alternatively, the system may be implemented in a single computer or a group of computers in a LAN or WAN.

As used herein, the words "may" and "may be" are to be interpreted in an open-ended, non-restrictive manner. At minimum, "may" and "may be" are to be interpreted as definitively including structure or acts recited.

Further, while flow charts presented herein illustrate a series of sequential blocks for exemplary purposes, the order of blocks is not critical to the invention in its broadest sense. Additionally, blocks may be omitted and others added without departing from the spirit of the invention. The invention may include combinations of features described in connection with differing embodiments.

For example, in the exemplary method, illustrated in flow chart 400 of FIG. 4, for generating a profile data set, step 408 may be removed. The profiles generated at step 406 may together form a profile data set. This profile data set may be used with a diagnostic method, dynamic surveying method, or other features and principles consistent with the present invention.

In another example, the profiles generated at step 406 may not include using a hierarchical clustering algorithm. The profiles, as illustrated in FIG. 13, generated before agglomeration by the hierarchical clustering algorithm may together form another profile data set. This profile data set may also be used with a diagnostic method, dynamic surveying method, or other features and principles consistent with the present invention.

In the foregoing description, various features are grouped together in various embodiments for purposes of streamlining the disclosure. This method of disclosure is not to be interpreted as reflecting an intention that the claimed invention requires more features than are expressly recited in each claim. Rather, as the following claims reflect, inventive aspects may lie in less than all features of a particular embodiment described above. Thus, the following claims are hereby incorporated into this description, with each claim standing on its own as a separate embodiment of the invention.

What is claimed is:

1. A dynamic survey method; comprising:
   accessing data organized by an artificial intelligence engine;
   accessing queries; and
   presenting to a subject a subset of queries from the accessed queries, wherein, for at least some of the queries presented, the method further comprises selecting a next query as a function of at least one answer to a previous query, and
   wherein the accessed data comprises information identifying characteristics and information for predicting evolution of the characteristics.

2. A dynamic survey method, comprising:
   accessing data organized by an artificial intelligence engine;
   accessing queries; and
   presenting to a subject a subset of queries from the accessed queries, wherein, for at least some of the queries presented, the method further comprises selecting a next query as a function of at least one answer to a previous query, and
   wherein the accessed data comprises a profile data set.

3. The method of claim 2, wherein at least one member in the profile data set is excluded based on the at least one answer to the previous query and the next query is selected to exclude at least one additional member in the profile data set.

4. The method of claim 3, wherein at least one member remaining in the profile data set is used to provide a diagnostic of the subject.

5. The method of claim 3, wherein at least one member remaining in the profile data set is used to provide advice to the subject.

6. The method of claim 3, wherein at least one member remaining in the profile data set is used to provide information to the subject.

7. A dynamic survey method, comprising:
   accessing data organized by an artificial intelligence engine;
   accessing queries; and
   presenting to a subject a subset of queries from the accessed queries, wherein, for at least some of the queries presented, the method further comprises selecting a next guery as a function of at least one answer to a previous guery, and
   wherein the next query is selected to narrow a portion of the accessed data.

8. The method of claim 2, wherein the next query is selected to narrow a portion of the profile data set.

9. The method of claim 8, wherein the next query is selected to present the fewest number of queries to the subject before using at least one member remaining in the profile data set to provide at least one of a diagnostic, advice, and information to the subject.

10. The method of claim 2, wherein during organization of the accessed data by the artificial intelligence engine, the artificial intelligence engine produces data representing modalities of characteristics in the accessed data.

11. The method of claim 10, wherein the data representing modalities of the characteristics is binary data.

12. The method of claim 11, wherein the data representing modalities is produced by the artificial intelligence engine using at least one of an unconstrained binary coding, additive binary coding, and disjunctive binary coding.

13. The method of claim 2, wherein during organization of the accessed data by the artificial intelligence engine, the artificial intelligence engine uses neighborhood data.

14. The method of claim 2, wherein the artificial intelligence engine uses at least one of a dynamic cluster method, k-means algorithm, and hierarchical clustering algorithm.

15. The method of claim 14, wherein the artificial intelligence engine uses neighborhood data.

16. The method of claim 1, wherein during organization of the accessed data by the artificial intelligence engine, the artificial intelligence engine produces data representing modalities of characteristics in the accessed data.

17. The method of claim 16, wherein the data representing modalities of the characteristics is binary data.

18. The method of claim 16, wherein the data representing modalities is produced by the artificial intelligence engine using at least one of an unconstrained binary coding, additive binary coding, and disjunctive binary coding.

19. The method of claim 7, wherein at least one of accessing the data, accessing the queries, and presenting the subset to the subject is performed over a network.

20. A dynamic survey method, comprising:
accessing data organized by an artificial intelligence engine;
accessing queries; and
presenting to a subject a subset of queries from the accessed queries,
wherein, for at least some of the queries presented, the method further comprises selecting a next query as a function of at least one answer to a previous query, and
wherein the accessed data is organized using neighborhood data.

21. A dynamic survey method, comprising:
accessing data organized by an artificial intelligence engine;
accessing queries; and
presenting to a subject a subset of queries from the accessed queries,
wherein, for at least some of the queries presented, the method further comprises selecting a next query as a function of at least one answer to a previous query, and
wherein the accessed data is organized using at least one of a dynamic cluster method, k-means algorithm, and hierarchical clustering algorithm.

22. The method of claim 21, wherein the accessed data is organized using neighborhood data.

23. The method of claim 7, wherein the next query is selected sequentially.

24. A dynamic survey method, comprising:
accessing data organized by an artificial intelligence engine;
accessing queries; and
presenting to a subject a subset of queries from the accessed queries, wherein, for at least some of the queries presented, the method further comprises selecting a next guery as a function of at least one answer to a previous guery, wherein the next guery is selected seguentially.
wherein at least one answer to at least one query is used to narrow a portion of the accessed data, and wherein the next query is selected sequentially and presented to the subject such that at least a portion of remaining accessed data is used to provide at least one of a diagnostic, advice, and information to the subject.

25. The method of claim 7, wherein the next query is selected sequentially through a sequence of queries.

26. The method of claim 7, wherein the artificial intelligence engine is at least one of a neural network, constraint program, fuzzy logic program, classification program, and logic program.

27. The method of claim 7, wherein the next query is selected to present the fewest number of queries to the subject before using at least one member remaining in the profile data set to provide at least one of a diagnostic, advice, and information to the subject.

28. A dynamic survey method, comprising:
accessing data organized by an artificial intelligence engine;
accessing queries; and
presenting to a subject a subset of queries from the accessed queries, wherein, for at least some of the queries presented, the method further comprises selecting a next query as a function of at least one answer to a previous query, and
wherein at least one of the queries is selected using an additional artificial intelligence engine.

29. The method of claim 7, wherein at least one of the queries is selected using the artificial intelligence engine.

30. The method of claim 7, wherein at least one answer to at least some of the queries are used to process at least some of the accessed data.

31. A system, comprising:
a data processor; and
a storage medium functionally coupled to the data processor, wherein the storage medium contains instructions to be executed by the data processor for performing the method of claim 24.

32. A computer program product, comprising a computer-readable medium, wherein the computer-readable medium contains instructions for executing the method of claim 24.

33. A system, comprising:
a data processor; and
a storage medium functionally coupled to the data processor, wherein the storage medium contains instructions to be executed by the data processor for performing the method of claim 7.

34. A computer program product, comprising a computer-readable medium, wherein the computer-readable medium contains instructions for executing the method of claim 7.

* * * * *